(12) United States Patent
Katoh et al.

(10) Patent No.: US 6,363,313 B1
(45) Date of Patent: Mar. 26, 2002

(54) FUEL PROPERTY DETECTING SYSTEM

(75) Inventors: Hiroshi Katoh; Shigeaki Kakizaki; Takane Hayashi, all of Yokohama (JP)

(73) Assignee: Nissan Motor Co., Ltd., Yokohama (JP)

(*) Notice: Subject to any disclaimer, the term of this patent is extended or adjusted under 35 U.S.C. 154(b) by 0 days.

(21) Appl. No.: 09/545,166

(22) Filed: Apr. 6, 2000

(30) Foreign Application Priority Data

Apr. 6, 1999 (JP) .......................................... 11-098709
Apr. 14, 1999 (JP) .......................................... 11-106659

(51) Int. Cl.$^7$ .............................................. F02D 41/14
(52) U.S. Cl. ........................................ 701/104; 701/109
(58) Field of Search ................................ 701/104, 109; 123/679–687, 1 A

(56) References Cited

U.S. PATENT DOCUMENTS 5,469,831 A * 11/1995 Takahashi ................... 123/680

FOREIGN PATENT DOCUMENTS

| JP | 64-3245 | 1/1989 |
| JP | 6-101529 | 4/1994 |
| JP | 7-63082 | 3/1995 |
| JP | 10-18882 | 1/1998 |
| JP | 10-18883 | 1/1998 |

* cited by examiner

*Primary Examiner*—Andrew M. Dolinar
(74) *Attorney, Agent, or Firm*—Foley & Lardner

(57) ABSTRACT

A fuel property detecting system comprises a control unit coupled to a fuel injector and an air-fuel ratio sensor. The control unit is arranged to sample data of a response waveform of an exhaust air-fuel ratio in response to an injected fuel quantity at a transient period, to identify a plant model as to fuel in use by controlling a parameter of a previously constructed plant model on the basis of the input and output data so as to decrease a prediction error between the plant model and a norm model, to calculate a cutoff frequency of the identified plant model, and to estimate a fuel property of the fuel in use from the calculated cutoff frequency of the identified plant model and data previous stored in the control unit.

37 Claims, 30 Drawing Sheets

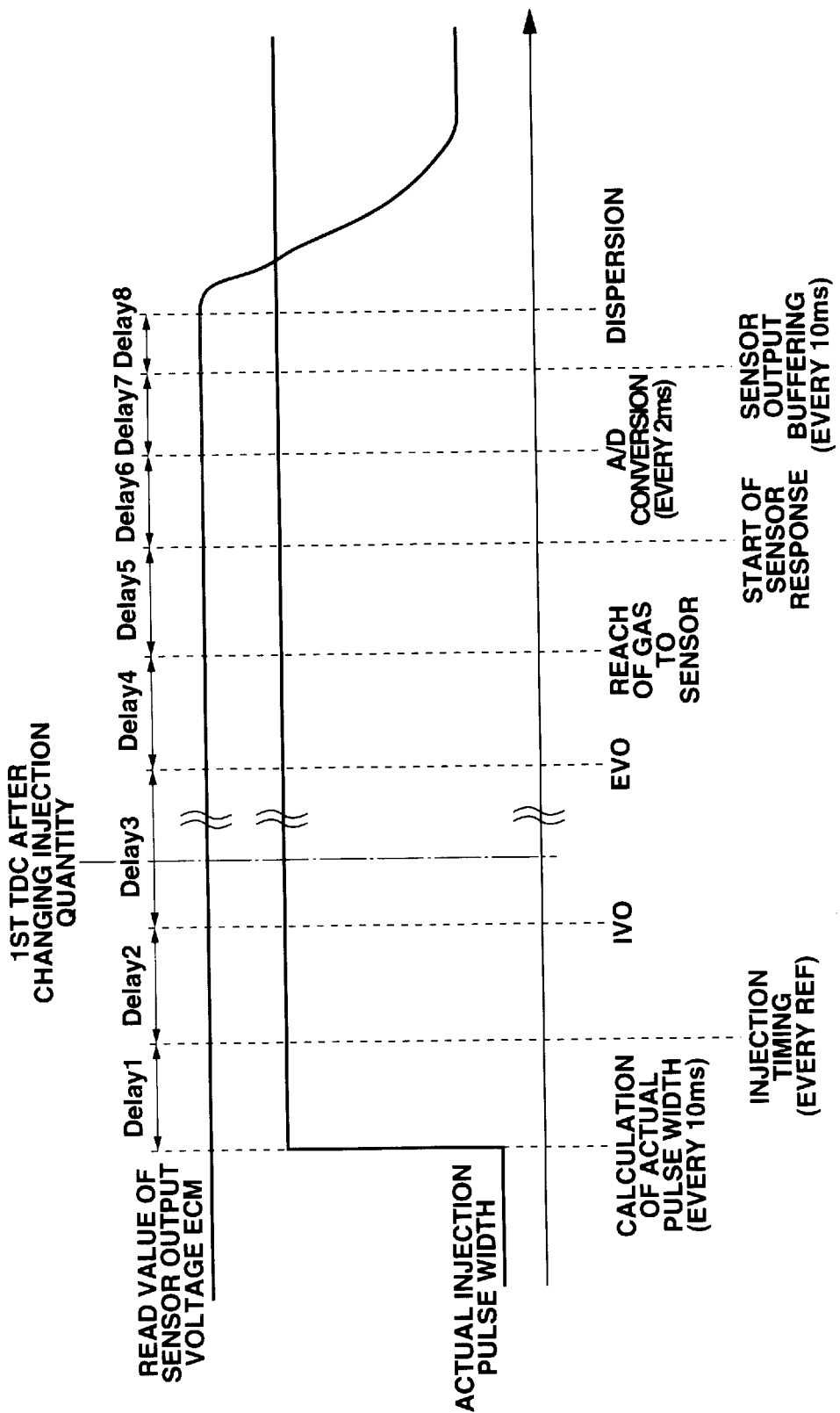

FIG.8

| ITEM DETERMINED FROM DRIVE CONDITION | ITEM DETERMINED FROM CALCULATION TIMING | ITEM FLUCTUATED BY DISPERSION |
|---|---|---|
| DELAY 3 : DELAY FROM IVO TO EVO<br><br>DELAY 5 : RESPONSE DELAY OF SENSOR | DELAY 1 : DELAY FROM INJECTION QUANTITY CALCULATION TO ACTUAL INJECTION START<br><br>DELAY 2 : DELAY FROM ACTUAL INJECTION START TO IVO<br><br>DELAY 6 : DELAY FOR A/D CONVERTING SENSOR OUTPUT AND STORING IT IN EMC<br><br>DELAY 7 : DELAY UNTIL BUFFERING SENSOR OUTPUT IN MEMORY | DELAY 4 : DELAY FROM EX. GAS DISCHARGE TO REACHING SENSOR<br><br>DELAY 8 : DISPERSION |

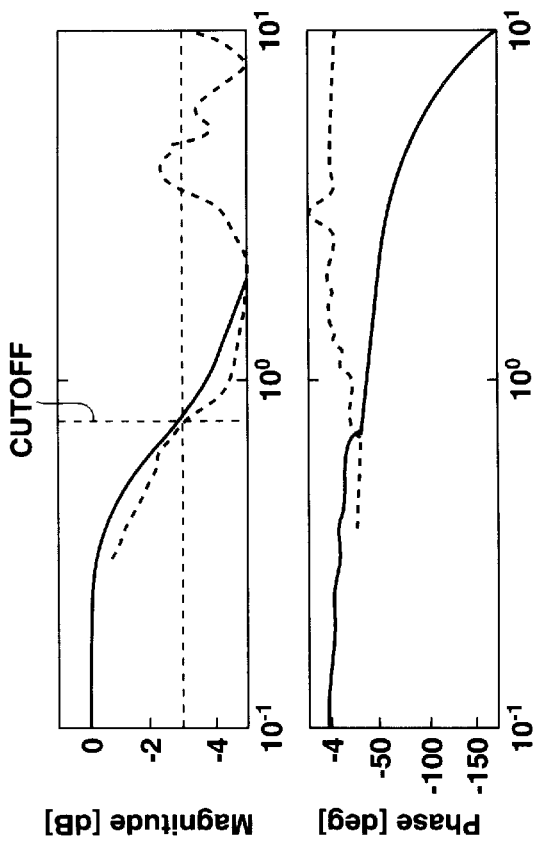
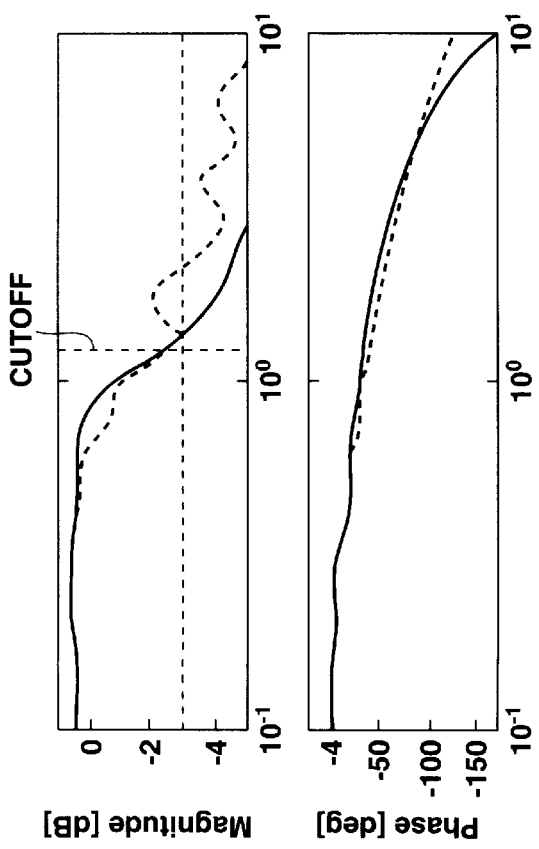

TMKAS MAP

TMKASS MAP

FUEL PROPERTY DETECTING SYSTEM

BACKGROUND OF THE INVENTION

The present invention relates to a fuel property detecting system, and more-particularly to a system for detecting a property of gasoline employed in an internal combustion engine.

In order to improve performances of an internal combustion engine, various corrections as to fuel injection quantity have been executed. Japanese Patent Provisional Publication No. 6-101529 discloses a fuel injection-quantity correction method for improving an operational stability of an engine during a warm-up period. Generally, a part of fuel injected from an injector is attached on a wall surface of an intake port and flows along the surface into each cylinder. The quantity of this wall-flow fuel is largely affected by a fuel property, particularly, by a volatility of fuel. Therefore, in order to stably operate engines against different volatilities of gasoline, various correction values of a fuel injection quantity are generally matched with heavy-most gasoline having the lowest volatility in practically used gasoline.

SUMMARY OF THE INVENTION

However, under a condition that such correction values for fuel injection quantity are matched with heavy-most gasoline, if lighter gasoline is used, the various correction values generally becomes too large and tend to put the air-fuel ratio into a rich side and to degrade exhaust emission, particularly, CO and HC.

It is therefore an object of the present invention to provide a fuel property detecting system which estimates a fuel property of fuel in use in order to properly adapt the correction values of fuel injection quantity according to fuel in use.

A fuel property detecting system according to the present invention for an internal combustion engine and comprises a fuel injector, an air-fuel ratio sensor and a control unit. The fuel injector is installed to the engine and injects a quantity of fuel to the engine. The air-fuel ratio sensor is installed to an exhaust passage of the engine and detects an exhaust air-fuel ratio. The control unit is coupled to the fuel injector and the air-fuel ratio sensor. The control unit is arranged to calculate the quantity of fuel injected from the fuel injector according to an operating condition of the engine, to command the fuel injector to inject the calculated quantity of fuel, to sample data of a response wave-form of the exhaust air-fuel ratio in response to the injected quantity of fuel at a transient period, to identify a plant model as to fuel in use by controlling a parameter of a previously constructed plant model on the basis of the sampled data so as to decrease a prediction error between the plant model and a norm model, to calculate a cutoff frequency of the identified plant model, and to estimate a fuel property of the fuel in use from the calculated cutoff frequency of the identified plant model and data previous stored in the control unit.

BRIEF DESCRIPTION OF THE DRAWINGS

In the drawings, same reference numerals denote same parts and elements throughout all figures.

FIG. 7 is a wave-form diagram representing a delay time between input and output.

FIG. 8 is a table showing classified delay times.

FIGS. 13A to 13D are Bode diagrams showing the identification result and an actual data.

DETAILED DESCRIPTION OF THE INVENTION

Referring to FIGS. 1 to 23, there is shown a first embodiment of a fuel property detecting system according to the present invention.

Figure 1:
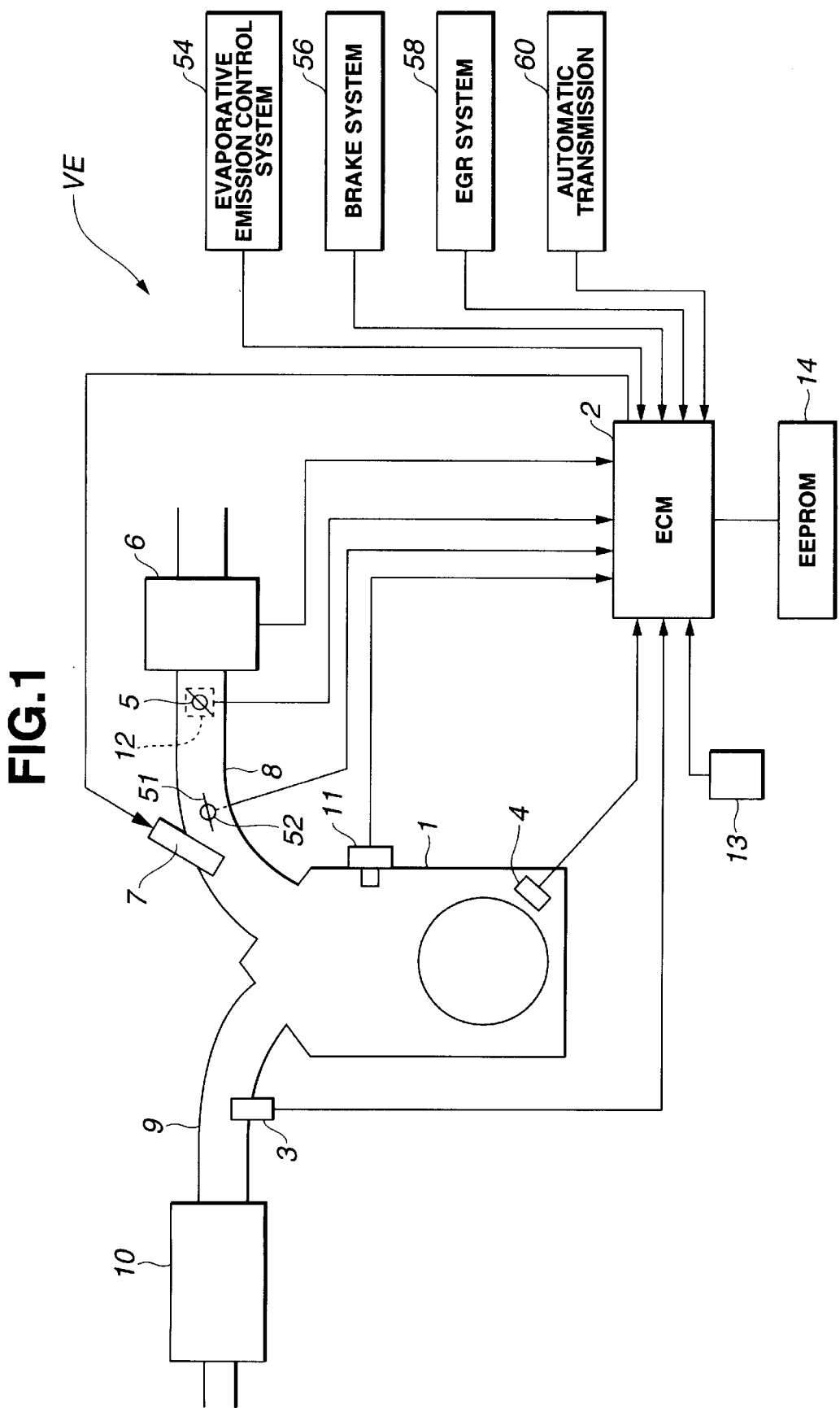
FIG. 1 is a schematic view showing a control system for an engine control in which a fuel property estimating system is included.

FIG. 1 shows the fuel property detecting system for an internal combustion engine 1 of an automotive vehicle VE. When the engine 1 is operating, intake air is supplied to each cylinder of the engine 1 through an air cleaner (not shown) and an intake pipe 8 according to an opening degree of a throttle valve 5 in the intake pipe and an engine operation condition. An electronic control module (ECM) 2 outputs a fuel injection signal to each fuel injector 7 installed to the intake pipe 8 so that each fuel injector 7 injects a quantity of fuel to each cylinder to adjust an air-fuel ratio according to the engine operating condition.

The ECM 2 is coupled to a crank angle sensor 4, an airflow meter 6, a wide-range air-fuel ratio sensor (A/F sensor) 3, a water temperature sensor 11 and a throttle sensor 12 to receive various signals indicative of the engine operating condition therefrom. More specifically, the crank angle sensor 4 outputs a REF signal indicative of an operating cylinder to the ECM 2. If a four cylinder engine 1 is employed in this embodiment, the crank angle sensor 4 outputs the REF signal by each 180° angle. If a four cylinder engine 1 is employed in this embodiment, the crank angle sensor 4 outputs the REF signal by each 120° angle. The ECM 2 calculates an engine rotation speed Ne on the basis of the REF signal. The airflow meter 6 is installed to the intake pipe 8 and outputs a signal indicative of an intake air quantity Qa to the ECM 2. The A/F sensor 3 is installed at a downstream side of a three-way catalytic converter 10 in an exhaust pipe 9 and outputs a signal indicative of an exhaust air-fuel ratio to the ECM 2. The water temperature sensor 11 is installed to the engine 8 and outputs a signal indicative of a coolant temperature Tw to the ECM 2. The throttle sensor 12 is installed to the throttle valve 5 and outputs a signal indicative of an opening degree of a throttle valve 5 to the ECM 2. The ECM 2 calculates a basic injection pulse width Tp on the basis of the intake air quantity Qa and the engine rotation speed Ne. When acceleration or deceleration of the vehicle VE is executed, a correction as to a wall-flow fuel is executed by adding a transient correction quantity Kathos to the basis injection pulse width Tp. The transient correction quantity Kathos is also added to the basic injection pulse width Tp when the engine 1 is started or when a target equivalence ratio Tfbya is changed. The quantity of the wall-flowing fuel is largely varied by starting the engine 1.

The ECM 2 is further coupled to an operation switch 52 connected to a swirl control valve 51, a brake system 54, an evaporative emission control system 56, an EGR (Exhaust Gas Recirculation) system 58, and an automatic transmission 60.

The ECM 2 executes a fuel correction control by using the target equivalence ratio Tfbya in order to improve a stability of the engine 1 at a cold start or to reply to a demand output under a high load condition of the engine 1. Further, the ECM 2 executes a selecting control of a lean air/fuel ratio and a theoretical air/fuel ratio according to a driving condition informed from the shift position signal from a shift position sensor 13 and a vehicle speed indicative signal from a vehicle speed sensor (not shown). The three-way catalytic converter 10 installed in an exhaust pipe 9 of the engine 1 is arranged to execute a deoxidization of NOx of exhaust gas and an oxidation of HC and CO of the exhaust gas so as to perform a maximum conversion efficiency during the theoretical air-fuel ratio operating condition. When the engine 1 is operating in the lean air-fuel ratio condition, the three-way catalytic converter 10 performs a preferable oxidation efficiency as to HC and CO and an insufficient deoxidization efficiency as to NOx.

If the air-fuel ratio is shifted to a lean side, the generation quantity of NOx is decreased. That is, if the air-fuel ratio is shifted to a predetermined lean air-fuel ratio, it becomes possible to decrease the generation quantity of NOx to a quantity which is as same as that treated by the three-way catalytic converter 10 and simultaneously the fuel consumption of the engine 1 is improved. Accordingly, in a predetermined range of a vehicle driving condition where the load of the engine 1 is not so large, a lean air-fuel ratio is maintained by setting the target equivalence ratio Tfbya at a value smaller than 1.0, and in the other vehicle operating condition the ECM 2 executes the control of adjusting the air-fuel ratio at the theoretical air-fuel ratio by setting the target equivalence ratio Tfbya at 1.0.

If the target equivalence ratio Tfbya is changed according to the change of the vehicle operating condition and if the transient correction quantity Kathos is calculated from Tfbya=1.0 (theoretical ratio), the air-fuel ratio is temporally shifted to an over-rich state or a over-lean state by the shortage of the transient correction quantity Kathos caused by changing the target equivalence ratio Tfbya, such as by the deceleration from the output air-fuel ratio range wherein the target equivalence ratio Tfbya is greater than 1.0. This temporal shifting of the air-fuel ratio degrades the following-up ability of the air-fuel ratio control. Therefore, in order to prevent this degradation, the ECM 2 is arranged to calculate a balanced deposit quantity Mfh by using the target equivalence ratio Tfbya as a parameter. More specifically, the ECM 2 employs the following equation to obtain the balanced deposit quantity Mfh.

$$Mfh = Avtp \times Mfhtvo \times Tfbya \times CYLNRN\#,$$

wherein Mfh is a total quantity of the balanced deposit quantity of all cylinders of the engine 1, Avtp is a pulse width corresponding to airflow quantity at fuel injector, Mfhtvo is a deposit magnification, and CYLDRN# is the number of cylinders of the engine 1. A further detailed explanation of this equation is disclosed in Japanese Patent Provisional Publication No. 10-18882. A deposit speed (a deposit quantity per a unit cycle) Vmf is calculated by multiplying a quantity rate Kmf with a difference between the balanced deposit quantity Mfh (balanced quantity of wall-flow fuel) and a deposit quantity Mf at a present time. That is, the deposit speed Vmf is calculated from the following equation by each cycle.

$$Vmf=(Mfh-Mf) \times Kmf$$

When the balanced deposit quantity Mfh is increased, for example, by the acceleration of the vehicle VE, the transient correction quantity Kathos is employed instead of the deposit speed Vmf for calculating an actual injection pulse width CTIn for each cylinder as follows:

$$CTIn=(Avtp \times Tfbya+Kathos) \times \alpha \times 2+Ts+Chosn^1,$$

wherein Kathos is the transient correction quantity for each cycle, $\alpha$ is a feedback correction coefficient of the air-fuel ratio, Ts is an invalid injection pulse width, and $Chosn^1$ is a correction quantity of a wall-flow fuel for each cylinder at every cycles. The actual injection pulse width CTIn applied to each fuel injector 7 is calculated when a sequential injection is executed. If the four-cylinder engine is employed in this embodiment, the sequential injection is executed once per two rotation of a crankshaft of the engine in the order of ignition order of the cylinders. The value by each cycle is a value per each input of 1REF signal. The value by each cylinder one cycle is a value of per each input of 4REF signal. A reference "n" of CTIn and $Chosn^1$ represents the number of each cylinder of the engine.

Hereinafter, the wall-flow correction quantity Chosn of each cylinder will be discussed. Generally, a wall-flow fuel includes a relatively low-speed response component in which an amount of fuel directly flowing into a cylinder is small (a low frequency component) and a high-speed response component in which an amount of fuel directly flowing into a cylinder is large and mainly accounted (a high frequency component). The deposit speed Vmf is a wall-flow correction quantity as to the low frequency component, and the wall-flow correction quantity Chosn is a correction quantity as to the high frequency component. That is, in order to take account of the high frequency component of the wall-flow fuel, the wall-flow correction quantity Chosn is employed. More specifically, when the airflow indicative pulse width Avtp is increasing, that is, during acceleration of the vehicle VE, by employing a variation $\Delta$Avtpn which is a variation of a pulse width Avtp corresponding to the airflow quantity at the fuel injector during a period from a previous injection to the present time, the wall-flow correction quantity Chosn is calculated from the following equation:

$$Chosn=\Delta Avtpn \times Gztwp,$$

wherein Gztwp is an increase gain.

On the other hand, when the airflow indicative pulse width Avtp is decreasing, that is, during deceleration, the wall-flow correction quantity Chosn is calculated from the following equation:

$$Chosn=\Delta Avtpn \times Gztwm,$$

wherein Gztwm is a decrease gain.

By adding the calculated wall-flow correction quantity Chosn of each cylinder to a fuel injection pulse width of simultaneous injection of corresponding cylinder, the wall-flow correction as to the high frequency component is executed. The increase gain Gztwp and the decrease gain Gztwm are employed for executing a correction as to a water temperature of the engine. A last character "n" of $\Delta$Avtpn represents the numbers of the cylinders of the engine 1 as is similar to that of CTIn.

Even if both of the wall-flow correction as to the low frequency component and the wall-flow correction as to the high frequency component are employed in the calculation of the fuel injection quantity, if Chosn is calculated without taking account of Tfbya, the air-fuel ratio is temporally shifted to an over-rich state or an over-lean state by the shortage of Chosn caused by the change of the target equivalence ratio Tfbya, such as by the deceleration from the output air-fuel ratio range. Therefore, the ECM 2 is arranged to calculate the high-frequency component wall-flow correction quantity Chosn by using the target equivalence ratio Tfbya as a parameter. More specifically, the ECM 2 employs the following equation to obtain the high-frequency component wall-flow correction quantity Chosn.

$$Chosn^1=(Kathos-Kathos_{-4Ref}) \times (Gztwc-1)/A,$$

wherein $Chosn^1$ is Chosn in the first cycle, $Kathos_{-4Ref}$ is Kathos in a previous cycle which is 4REF signal before the present cycle, Gztwc is the increase gain Gztwp or decrease gain Gztwm, and A is a first-cycle response gain of the low frequency component. Further, the fuel recovery may be taken into consideration for the further optimum wall-flow correction quantity. That is, when the engine 1 is operating during the fuel recovery caused by the change of the target equivalence ratio Tfbya, the wall-flow correction quantity (Chosn1 and Vmf are calculated upon taking account of the fuel cut which include a case of a fuel cut by each cylinder and a case of a fuel cut to all cylinders. A detailed explanation of this correction is disclosed in Japanese Patent Provisional Publication No. 10-18882.

On the other hand, when the engine 1 is started in a cold condition, that is, when a so-called cold start is executed, the fuel injection quantity is increased by an post-start increase correction coefficient KAS so as to set the air-fuel ratio at a rich value richer than the theoretical air-fuel ratio. This control stables the engine operation during the cold start period. A further detailed explanation of this control is disclosed in Japanese Patent Provisional Publication No. 6-101529. For example, the post-start increase correction coefficient KAS is calculated from the equation (36) of KAS=TKAS×TNKAS+KASS. Accordingly, a line indicative of KAS is generally decreased linearly from an initial value corresponding to a value at the turning-on of the start switch by a steep slope steeper than that at OFF timing of the starter switch, and changes its slope to a slow slope, and finally takes a value of 0.

The post-start increase correction coefficient KAS is a part of the target equivalence ratio Tfbya. That is, the target equivalence ratio Tfbya is calculated by the following equation:

$$Tfbya=Kml+KAS,$$

wherein Kml is an air-fuel ratio correction coefficient. The air-fuel ratio correction coefficient Kml is employed for determining the target air-fuel ratio according to the drive condition, and is obtained by retrieving a map which has parameters of the rotation speed and the load of the engine 1. When the target air-fuel ratio is changed, the map value of Kml is retrieved, and a predetermined damper operation is executed.

When the engine 1 is started, a special fuel injection pulse width TIST is set. The detailed explanation of this setting is disclosed in Japanese Patent Provisional Publication No. 7-63082. When the large torque is required, such as, when the radical acceleration is executed, an acceleration interruption injection pulse width IJSETn is calculated, and sometimes an interruption injection is executed during the simultaneous injection.

The reason for executing the above-mentioned various corrections for the fuel injection quantity is that a fuel supply delay as to the wall-flow delay is generated. The quantity of the wall-flow fuel is further dependent on a fuel property and particularly on a volatility of the employed fuel. That is, the quantity of the wall-flow fuel is increased according to the decrease of the volatility of fuel. Therefore, conventional systems are arranged to execute the correction control of the fuel injection quantity so that even when heavy-most gasoline is employed, the engine operation during a cold condition is kept stable by properly determining table values employed in the calculation of KAS.

However, when a lighter fuel, which has a higher volatility than the heavy-most fuel has, is employed, the various correction quantities of the fuel injection quantity become too large, and therefore the actual air-fuel ratio becomes richer lo than the target value expected under a condition that heavy-most gasoline is employed. As a result, the exhaust emission employing the lighter gasoline is degraded. Particularly, as to CO and HC, the exhaust emission is degraded.

At a transient period and within a range where the quantity of the wall-flow fuel is large, the ECM 2 executes the following processes:

A: The ECM 2 executes sampling of a response waveform of the exhaust air-fuel ratio with respect to the fuel injection quantity.

B: The ECM 2 identifies a previously constructed plant model by adjusting parameters of the plant model so as to minimize an estimation error of the parameters with respect to a norm model.

C: The ECM 2 obtains a cutoff frequency of the plant mode on the basis of the adjusted parameters.

D: The ECM 2 estimates the fuel property by comparing the obtained cutoff frequency with a cutoff frequency of the norm model which is a plant model as to reference fuel (Ref fuel).

E: The ECM 2 calculates the correction quantities according to the estimated fuel property.

Hereinafter, with reference to a block diagram of FIG. 2, an optimizing control executed by the ECM 2 will be discussed.

Figure 2:
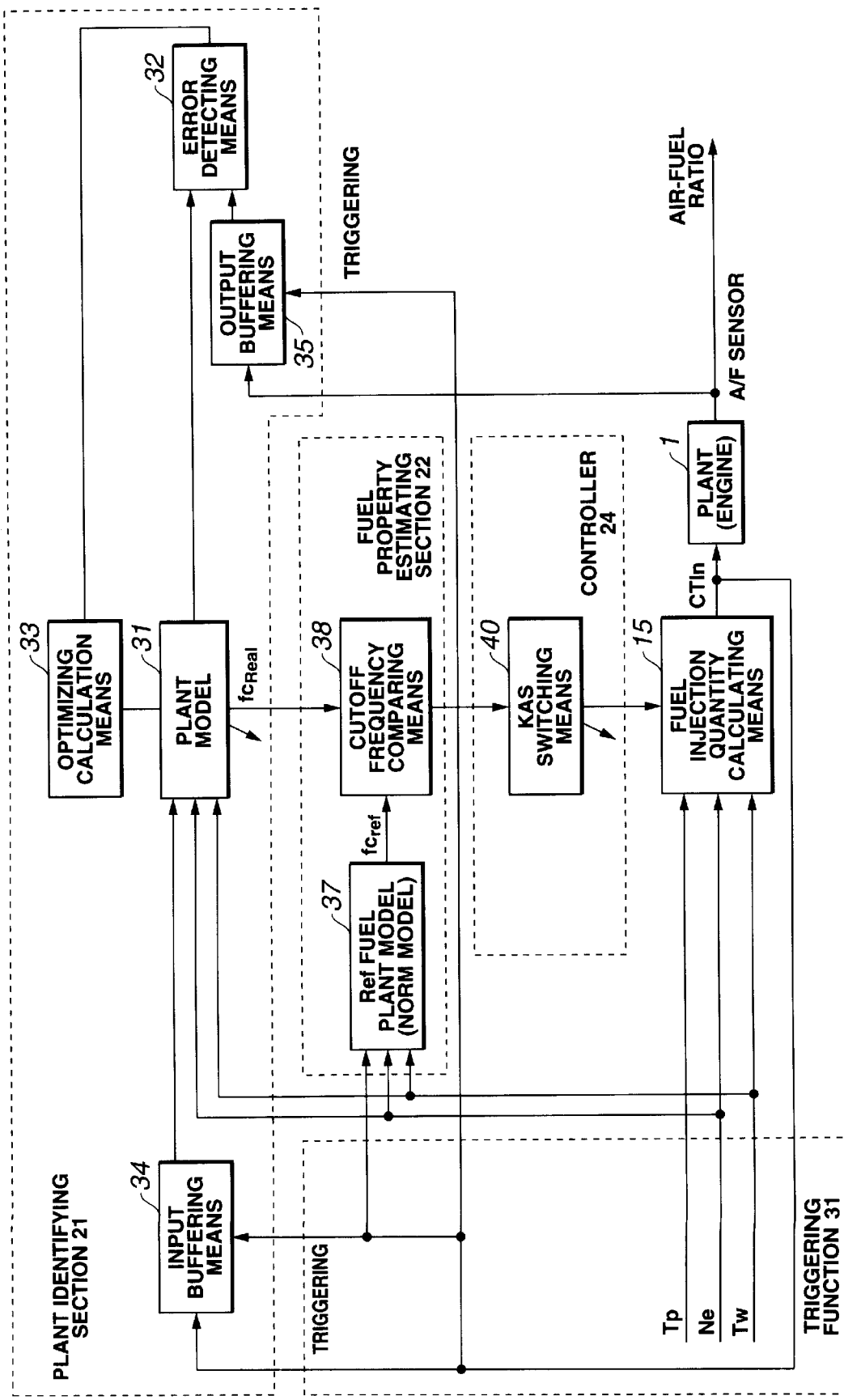
FIG. 2 is a block diagram showing a control system relating an estimation of fuel property.

FIG. 2 shows a control system of the optimizing control employed in the fuel property detecting system of the first embodiment according to the present invention. The control system comprises a plant identifying second 21, a fuel property estimating section 22, a triggering section 23 and a controller 24.

The plant identifying section 21 comprises a plant model 31, an error detecting means 32, an optimizing calculation means 33, an input (actual injection pulse width) buffering means, and an output (exhaust air-fuel ratio) buffering means 35. The plant identifying section 21 executes sampling of the actual injection pulse width CTIn and an output voltage of the A/F sensor 3 in response to a trigger decided by an engine parameter. Further, the plant identifying section 21 employs the sampled data as input and output signals of the plant model 31 to create a predetermined area and executes the identification of the plant model 31 in the created area. The form (degree) of the model has previously been determined from a physics model, and therefore the model parameter is optimally adapted with respect to the actual input and output signals.

The plant model 31 is a discrete-system cascade-coupling model wherein a fuel behavior characteristic is expressed by a second order delay model including a secondary denominator and a secondary numerator and an exhaust dynamic characteristic is expressed by a primary delay model including a primary denominator. That is, the plant model 31 is expressed by a physics model including a tertiary denominator and a tertiary numerator. The identification method employed in this embodiment is a batch processing east-square method employing ARX model.

The fuel property estimating section 22 comprises a norm model 37, which is a plant model as to reference fuel (Ref fuel), and a cutoff frequency comparing means 38. The fuel property estimating section 22 decides the fuel property by comparing the cutoff frequency $fc_{Real}$ of the plant model identified at the plant identification section 21 and a cutoff frequency $fc_{Ref}$ of the norm model 37 at the cutoff frequency comparing means 38.

In order to facilitate the explanation of this plant identification, as to a case in that two kinds of fuel (heavy gasoline, which are a low volatility fuel, and light gasoline, which is a high volatility fuel) are employed, the plant identification process will be discussed.

When a norm model matched with heavy gasoline is employed and when the cutoff frequency of the identified plant model 31 is higher than that of the norm model, it is decided that the gasoline in use is light gasoline. The reason for this is that since a fuel transfer delay of light gasoline is smaller than that of heavy gasoline, light gasoline performs a higher fuel responsibility as compared with heavy gasoline and maintains a predetermined response gain to a high frequency range as compared with heavy gasoline. Before the estimation of fuel property, a decision value for deciding fuel property has been initially set at a value corresponding to heavy gasoline.

The optimizing control of this first embodiment is arranged to execute the estimation of fuel property once during one trip period corresponding to a period from start to stop of the engine 1. The estimation result is stored in a nonvolatile memory (EEPROM) 14, and the stored date is referred in the next fuel control in the next trip (next engine start).

The triggering function 23 is arranged to sample input and output signals necessary for identifying a plant and to decide a condition for generating a trigger at which the plant identification is started.

In order to identify a system, generally it is necessary to obtain an input signal including wide-range frequencies. In the case of an engine, it is not substantive to generate an input of M-sequence signal. Therefore, a point, at which an input is steppedly changed, is determined as a sampling trigger. Further, conditions, which largely affect the behavior of fuel, such as EGR (Exhaust Gas Recirculation) and a swirl control should be omitted from a period for sampling data. Accordingly, it is necessary to decide that the above mentioned conditions exists or to generate an input signal for identification.

The controller 24 is arranged so that a post-start increase correction coefficient control means determines the post-start increase correction quantity KAS employed in the next trip at a proper value according to the fuel property estimated in the present trip. The controlled items as to KAS are an initial value and a damping rate (ratio).

Although the explanation of the fuel property detecting system in this embodiment will be done as to a two-value switching method, that is, as to selecting one of heavy gasoline and light gasoline, the number of selected values may be determined according to a distinguish performance of the fuel property and a demand of the engine 1. In case of the two-value switching method, the post-start increase correction coefficient control means is replaced with a post-start increase correction coefficient switching means 40. The fuel injection quantity calculating means 15 is arranged to calculate Vmf, CTIn and Chosn$^1$.

Next, the identification of the plant model 31 will be discussed in detail.

1. Plant Model

Figure 3:
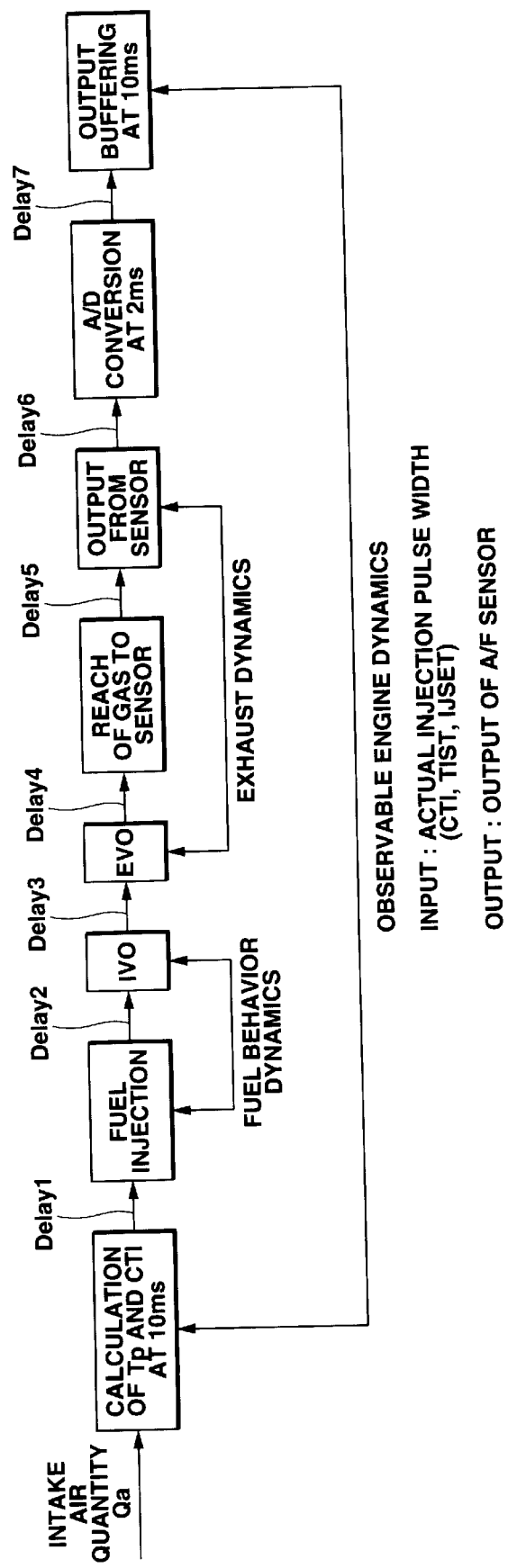
FIG. 3 is a block diagram showing an engine plant model.

It is necessary to extract only a dynamics of fuel behavior from a dynamics of the engine 1, in order to estimate the fuel property. FIG. 3 shows a model of a dynamics of a four-cycle engine (plant). Detectable input and output of the plant are the actual injection pulse width CTIn and the output value of the A/F sensor 3. The actual injection pulse width CTIn is obtained by calculating the basic injection pulse width Tp on the basis of the airflow quantity Qa and by correcting the obtained basic pulse width Tp through various correction values. The actual injection pulse width CTIn is replaced with a start injection pulse width TIST when the engine 1 is started, and is replaced with a acceleration interruption injection pulse width IJSETn when the vehicle VE is accelerated.

The plant model obtained from these input and output are constituted by 1.1; a fuel behavior model (dead time+delay system), 1.2; an exhaust model (dead time+delay system), and 1.3; a dead time caused by various calculations and combustion cycle.

1.1 Fuel Behavior Model

Figure 4:
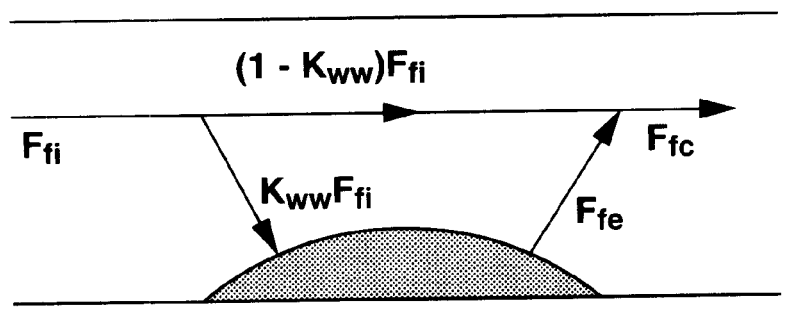
FIG. 4 is a schematic modeled view showing a model of fuel behavior.

Behavior of fuel injected from the injector 7 is modeled into a model shown in FIG. 4. This model is expressed by the following equations (1-1), (1-2) and (1-3).

$$F_{fc} = (1 - k_{ww}) \cdot F_{fi} + F_{fc} \quad (1\text{-}1)$$

$$F_{fe} = e^{-t/TWW} \cdot k_{ww} \cdot F_{fi} / T_{ww} \quad (1\text{-}2)$$

$$G_{ww}(S) = (1 - k_{ww}) + k_{ww}/(sT_{ww} + 1), \quad (1\text{-}3)$$

wherein Gww is a transfer function of fuel behavior, Ffi is a fuel injection part, Ffe is a fuel evaporation part, Ffc is a cylinder intake fuel part, kww is a deposit rate, and Tww is a time constant of evaporation.

This mathematical model is represented by one time constant Tww and one gain kww. However, the behavior of fuel is generally expressed by a time constant due to deposition and evaporation of fuel and a time constant due to cylinder intake delay. A low-speed response part is a low frequency component, and a high-speed response part is a high frequency component. Therefore, in order to adapt to these two kinds of fuels which are different in response, by coupling the mathematical model of the equations (1-1), (1-2) and (1-3), the adapted model is obtained as follows:

$$G_{ww}(s) = (1 - k_1 - k_2) + k_1/(sT_1 + 1) + k_2/(sT_2 + 1) \quad (2\text{-}1)$$

$$G_{ww}(z) = (1 - k_1 k_2) + k_1 \cdot (1 - e^{-Tsample/T1})/(z - e^{-Tsample/T1}) + k_2 \cdot (1 - e^{-Tsample/T2})/(z - e^{-Tsample/T2}) \quad (2\text{-}2)$$

$$G_{ww}(z) = (1 - B_1 - B_2) + B_1 \cdot (1 - A_1)/(z - A_1) + B_2 \cdot (1 - A_2)/(z - A_2) \quad (2\text{-}3)$$

wherein Tsample is a sampling cycle (a cycle for sampling the air-fuel ratio), $T_1$ is a time constant of the low frequency component, $T_2$ is a time constant of the high frequency component, $k_1$ is a gain of the low frequency component, $k_2$ is a gain of the high frequency component, $A_1$ is $e^{-Tsample/T1}$, $A_2$ is $e^{-Tsample/T2}$, $B_1$ is $k_1$, and $B_2$ is $k_2$.

Figure 5:
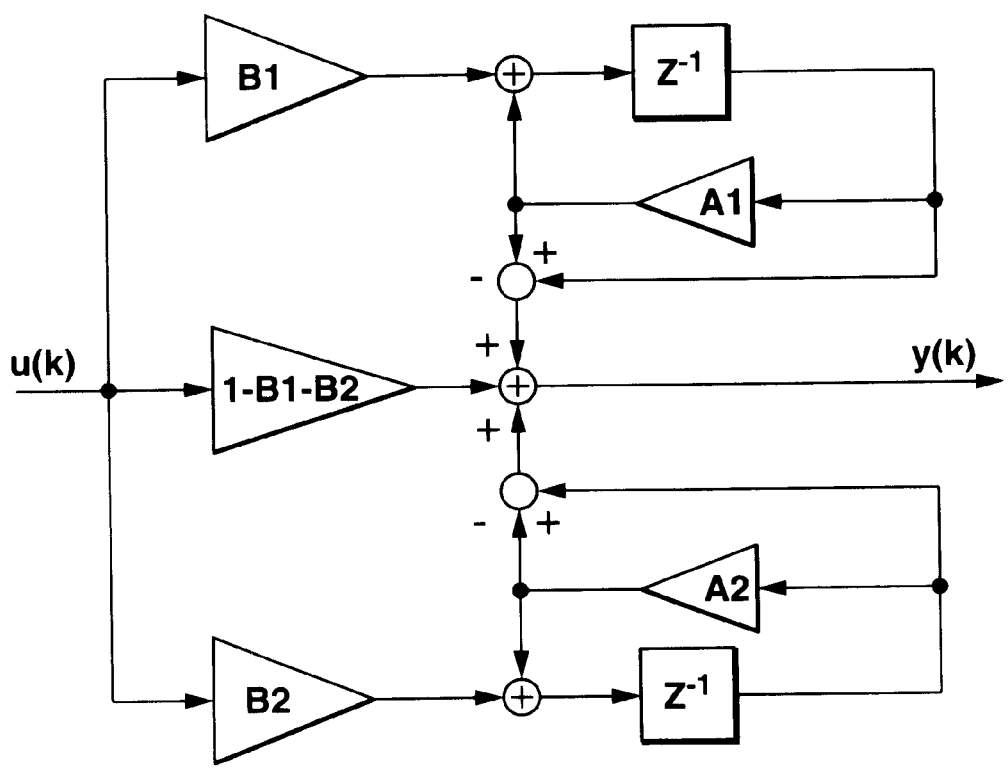
FIG. 5 is a block diagram showing a parallel pass representing the fuel behavior of FIG. 4.

The equation (2-2) is obtained by converting the equation (2-1) of a continuous system to a discrete system. The equation (2-3) is obtained by substituting $z = e^{sTsample}$ into the equation (2-2) and rearranging the equation. FIG. 5 shows a block diagram expressing the equation (2-3).

In this embodiment, it is defined that the dead time according to the fuel behavior is not included in the mathematical model of the fuel behavior, and the output signal is offset in time series. By this arrangement, the increase of the model degree is suppressed. The detailed explanation of this operation will be discussed later.

1.2 Exhaust Model

Figure 6:
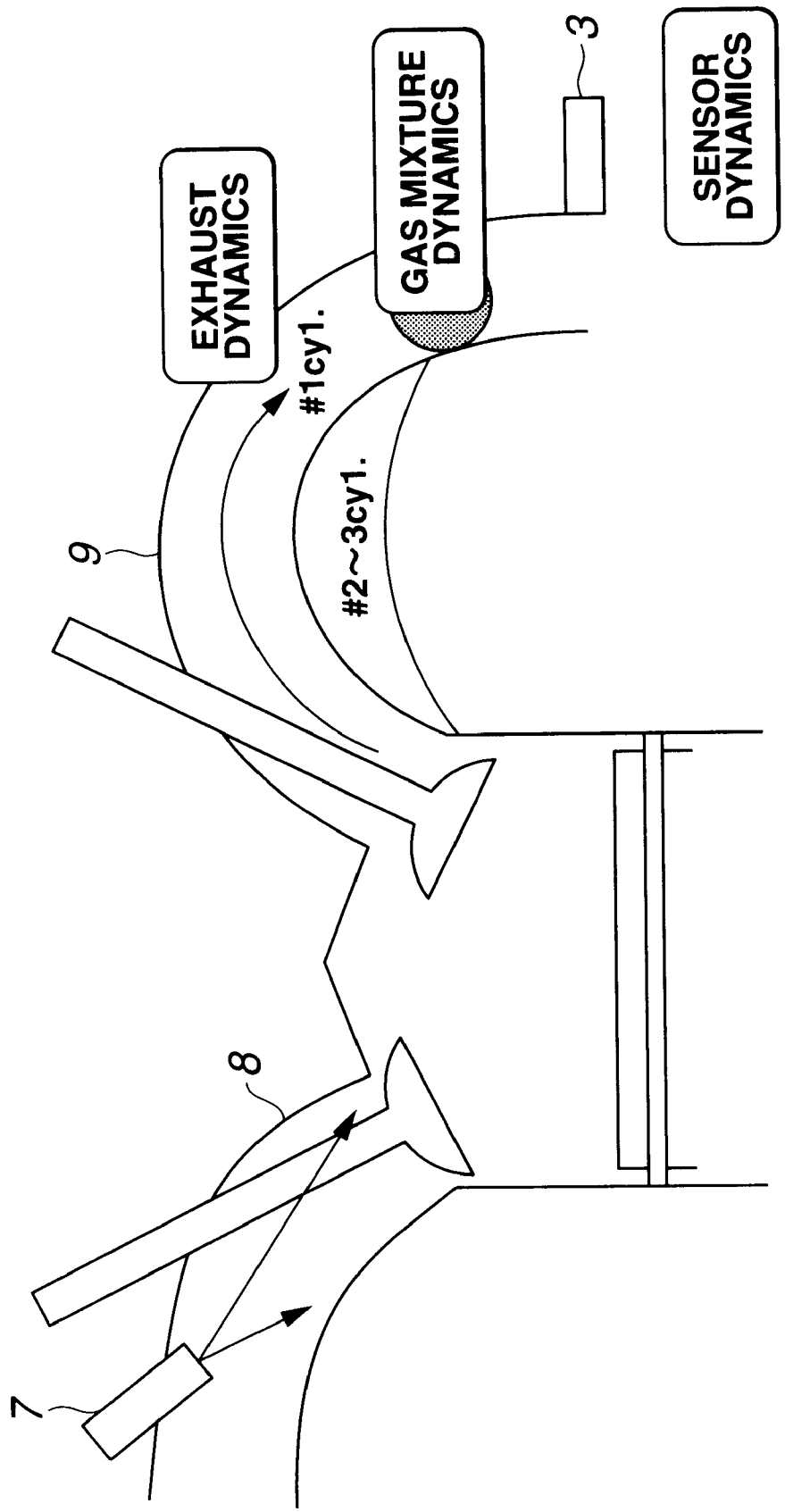
FIG. 6 is a schematic model view showing an exhaust model.

It is supposed that an exhaust model is constituted by an exhaust dynamics of each cylinder, a gas mixture dynamics at the exhaust manifold corrector portion and a sensor characteristics, as shown in FIG. 6. By combining these three elements of the exhaust model, it is designated by a physics model represented by "dead time+delay system". It is further supposed that the delay system is presented by "an exhaust gas transfer delay+a gas mixture delay+a sensor response delay", and each of them is a model having a degree equal to or greater than a primary degree. Since the plant model is identified by the ECM 2 equipped on the vehicle VE, it is necessary to suppress the degree of the models, and therefore the exhaust model is representatively expressed by a time constant as follows:

$$G_{ex}(s) = 1/(sT_{ex} + 1) \quad (3\text{-}1)$$

$$G_{ex}(z) = (1 - e^{-Tsample/Tex})/(z - e^{-Tsample/Tex}) \quad (3\text{-}2)$$

$$G_{ex}(z) = (1 - A_3)/(z - A_3), \quad (3\text{-}3)$$

wherein $G_{ex}$ is a transfer function of an exhaust dynamic characteristic, $T_{ex}$ is a time constant of evaporation, Tsample is a sampling cycle, and $A_3$ is $e^{-Tsample/Tex}$.

As is similar to the equations (2-1), (2-2) and (2-3), the equation (3-2) is obtained by converting the equation (3-1) into a discrete system. The equation (3-3) is obtained by substituting $z = e^{sTsample}$ into the equation (3-2) and rearranging the equation.

It is defined that the dead time as to the exhaust gas is not included in the mathematical model of the exhaust model, and that the output signal is offset in time series. By this arrangement, the increase of the model degree is suppressed. The detailed explanation of this operation will be discussed later.

1.3 Dead Time Model

The plant model 31 includes several dead times until a time that the ECM 2 reads the output value of the A/F sensor after the calculation of the actual injection pulse width CTIn as shown in FIG. 3 since the plant model 31 employs the actual injection pulse width CTIn as an input and the voltage read value of the output of the A/F sensor as an output. FIG. 7 shows these dead times during the input and output period in detail. In FIG. 7, the dead times are represented by "Delay" in detail.

Delay1: This dead time corresponds to a delay from the calculation of the fuel injection and the actual fuel injection start timing. The actual injection pulse width CTIn is calculated at 10 ms intervals, and therefore it is not certain that the pulse width is as same as that in every cycle until the timing that the fuel is actually injected. Accordingly, the dead time Delay1 is obtained by calculating a time period from the moment (timing) of the calculation of the pulse width on the basis of the angle of the injection start timing calculated and the engine rotation speed at this moment.

Delay2: This dead time corresponds to a delay from the actual injection start timing to intake valve open (IVO) timing. This dead time Delay2 is a time period that the fuel is injected and the injected fuel is supplied to a cylinder according to the intake valve open (IVO). This dead time Delay2 is determined from the fuel behavior characteristic and is set based on the vehicle operating condition and the fuel property. For example, the dead time Delay2 is determined at a proper value by employing an intermediate fuel having an intermediate volatility from commercial fuels and by actually measuring actual response times according to the stepped changes of the engine rotation speed and the load.

Delay3: This dead time corresponds to a delay from IVO to EVO (exhaust valve open), that is, a period including (intake→compression→combustion→exhaust). This dead time Delay3 is a time period during that the fuel is supplied into the cylinder through the intake valve and the combustion gas is discharged from the exhaust valve. The dead time Delay3 is obtained form the engine rotation speed and a profile of a cam mechanism, that is, from the design specification of the engine 1.

Delay4: This dead time corresponds to a delay from a timing that the combustion gas is discharged through an exhaust valve to a timing the exhausted combustion gas reaches the A/F sensor 3. This dead time Delay4 is determined by the flow speed of the exhaust gas depending on the engine rotation speed and the load and the length of the exhaust pipe 9 and the attached position of the A/F sensor 3. This may be obtained from the vehicle operating condition and the specification of hardware although the calculation thereof is complicated.

Delay5: This dead time corresponds to a sensor response delay. This dead time Delay5 is a time period from a timing that the exhaust gas reaches the A/F sensor 3 to a timing that the A/f sensor 3 outputs a signal (voltage). Although the A/F sensor 3 quickly reacts to the fluctuation of the oxygen quantity at several mil seconds (ms), a sensor cover of the A/F sensor 3 generates a delay of the gas mixing and the gas mixing delay mainly affects the responsibility of the A/F sensor 3 as a whole. The gas mixing delay is, therefore, largely affected by the shape of the sensor cover. Therefore, the sensor response delay Delay5 is properly set as is the same as the dead time Delay 4.

Delay6: This dead time corresponds to a time period for A/D converting the sensor output and storing the converted data in the ECM 2. More specifically, this dead time Delay6 is a period necessary for that the ECM 2 reads and stores the outputted voltage of the A/F sensor 3 through the A/D conversion of the outputted voltage. The system is arranged to execute this A/D conversion at 2 ms intervals, and therefore the maximum dead time is 2 ms.

Delay7: This dead time corresponds to a delay for buffering the sensor output in the memory. When the output of the A/F sensor 3 is sampled at 10 ms intervals, the maximum dead time may take 10 ms due to the sampling timing. Therefore, a period from the response start calculated from the A/D conversion value at 2 ms intervals to the sampling timing is treated as the dead time Delay7.

Delay8: This dead time corresponds to dispersion. The dead time Delay8 is a dead time except for the dead times Delay1 to Delay7. This dead time Delay8 includes dispersion among individuals and dispersion due to adaptation, and is not constant in every operation. Therefore, this dead time Delay8 is determined by determining the rising-up of the air-fuel signal after the dead times Delay1 to Delay7 elapsed.

The above-mentioned dead times Delay1 to Delay8 can be classified into (1) a class determined from the drive condition, (2) a class determined from the calculation timing, and (3) a class determined from the fuel property as shown in Table of FIG. 8. Therefore, the actual dead time is represented by the following equation:

Dead Time=Adaptation Term+Calculation Term+Decision Term, wherein Adaptation Term includes delays determined from the drive condition and retrieved from table and map, Calculation Term includes delays determined from the calculation timing and calculated from timing signal, and Decision Term includes delays properly determined according to the fluctuation of various dispersion such as fuel property.

2. Identification of Plant Model
2.1 Preparation of Identified Model

Although an engine actually performs non-linear characteristics strongly, in this control it is assumed that the engine 1 is a linear time-invariant system (LTI system) where the engine 1 performs linear and time-invariant at an adjacent area of an operating point. Further, in order to represent the input and output of the discrete time-series LTI system within a time area instead of Z area, a shift operator $q^{-1}$ is defined as follows:

$$q^{-1}x(k)=x(k-1), \qquad (4)$$

wherein (discrete time)=kT (T: sampling cycle, K=0, 1, 2, ...).

A system transfer function of the input u(t) and the output y(t) in the discrete system is represented by using the equation (4) as follows:

$$y(k)=G(q,\theta)\cdot u(k), \qquad (5)$$

wherein $\theta$ is constituted by a parameter for representing the model. However, the equation (5) represents based on ideal input and output. If external noise is taken into consideration, the system transfer function is represented as follows:

$$y(k)=G(q,\theta)\cdot u(k)+H(q,\theta)\cdot w(k), \qquad (6)$$

wherein $H(q,\theta)$ is a noise model.

Figure 9:
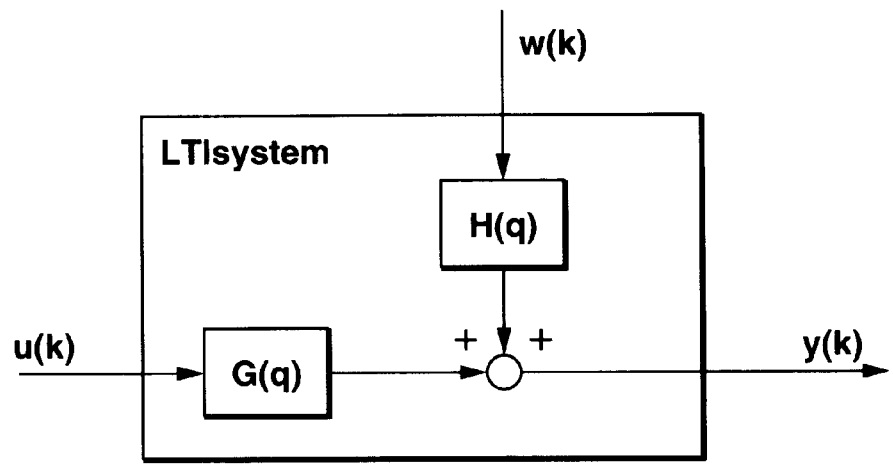
FIG. 9 is a block diagram showing a general LTI system.

Therefore, the equation (6) represents a common form of a discrete time-series LTI system. FIG. 9 shows a block diagram showing this discrete time-series LTI system.

The transfer function G(q) in this system is a product of the equation (2-3) and the equation (3-3), and the equation represented by Z-1 is represented by shift operator q-1 as follows:

$$G(q,\theta)=(1-A_3)\cdot\{q^{-1}(1-B_1-B_2)+$$
$$q^{-2}(B_1-A_1+B_2-A_2+A_1B_2+A_2B_1+$$
$$q^{-3}(A_1A_2-A_1B_2+A_2B_1)\}/\{1+q^{-1}(-A_1-A_2+A_3)+$$
$$q^{-2}(A_1A_2+A_2A_3+A_3A_1)-q^{-3}(A_1A_2A_3)\}. \qquad (7)$$

If the transfer function G(q) of this system is defined by the following equation (8):

$$G(q,\theta)=B(q,\theta)/A(q,\theta), \qquad (8)$$

the output y(k) of this system is represented as follows:

$$y(k,\theta)=\{B(q,\theta)/A(q,\theta)\}\cdot u(k)+H(q,\theta)\cdot w(k) \tag{9}$$

That is, as an identification model, a combined model of the plant model D(q) and a noise model H(q) is employed.

2.2 Identification Method

In a discrete time-series LTI system defined by the equation (6), a one-step future prediction value $y(k|\theta)$ of the output y(k) based on the input and output data detected by the time (k-1) is represented as follows:

$$y(k|\theta)=[1-H^{-1}(q,\theta)]y(k)+H^{-1}(q,\theta)G(q,\theta)u(k). \tag{10}$$

From this equation (10), the output at time k is expressed by data obtained until the time (k-1). Accordingly, a prediction error $\epsilon(k|\theta)$ is expressed as follows:

$$\epsilon(k|\theta)=y(k)-y(k|\theta). \tag{11}$$

In order to estimate the parameter, an evaluation norm $J_N(\theta)$ is determined as follows:

$$J_N(\theta) = \frac{1}{N}\sum_{k=1}^{N} l(k, \theta, \varepsilon(k, \theta)), \tag{12}$$

wherein the function $l(k, \theta, \epsilon(k,\theta))$ is an arbitrary scalar function for measuring a magnitude of the prediction error $\epsilon(k,\theta)$. According to the utilization of the identification result, it is decided what norm should be selected (square norm or logarithmic likelihood). By defining such an evaluation norm, the estimate $\theta(N)$ of an unknown parameter $\theta$ is determined. That is, the parameter $\theta$ is obtained so as to satisfy the following equation (13):

$$\theta(N) = \arg\min_{\theta} J_N(\theta). \tag{13}$$

Although various identification methods have been proposed commonly, an operation of an engine is an intermittent event including combustion cycle and is a controlled object tending to be a non-linear characteristic. However, in order to facilitate an algorithm of the control in this embodiment, it is assumed that the operation executed in the vicinity of the operating point is the LTI system.

Upon taking account of the quantity of the calculations, the accuracy of the identification, and anti-disturbance performance, herein a representative method "a batch identification method employing ARX model" is employed.

2.3 Identification Method employing ARX Model

The ARX model is called as an expression error model, and therefore this equation of this model includes a disturbance term e(k) in the right side of the following differential equation (14):

$$y(k)+a_1\cdot y(k-1)+\ldots+a_{na}\cdot y(k-na) = b_1\cdot u(k-1)+\ldots+b_{nb}\cdot y(k-nb)+e(k); \tag{14}$$

A parameter vector $\theta$ for expressing the model is represented as follows:

$$\theta=[a_1,\ldots,a_{na},b_1,\ldots,b_{nb}]^T. \tag{15}$$

If the data vector (regression vector) $\psi(k)$ is defined as follows:

$$\psi(k)=[-y(k-1),\ldots,-y(k-na), u(k-nb)]^T, \tag{16}$$

the output y(k) is represented as follows:

$$y(k)=\theta^T\psi(k)+w(k). \tag{17}$$

If the one-step future prediction value $y(k,\theta)$ of ARX model is obtained from the equation (10), the value is linear with respect to $\theta$ and is represented as follows:

$$y(k|\theta)=\theta^T\psi(k). \tag{18}$$

At this time, the prediction error $\epsilon(k,\theta)$ is represented as follows:

$$\epsilon(k,\theta)=y(k)-\theta^T\psi(k). \tag{19}$$

If the least squares method is applied to this linear regression model, the scalar function $l(k,\theta,e(k,\theta))$ is represented as follows:

$$l(k,\theta,\epsilon(k,\theta))=\epsilon^2(k,\theta). \tag{20}$$

The evaluation norm $J_N(\theta)$ for the parameter estimation is represented as follows:

$$J_N(\theta) = \frac{1}{N}\sum_{k=1}^{N}\varepsilon^2(k,\theta) = \frac{1}{N}\sum_{k=1}^{N}\{y(k)-\theta^T\psi(k)\}^2. \tag{21}$$

Further, the equation (21) is expressed as follows:

$$J_N(\theta) = \frac{1}{N}\sum_{k=1}^{N}y^2(k) - 2\theta^T\frac{1}{N}\sum_{k=1}^{N}y(k)\psi(k) + \theta^T\frac{1}{N}\sum_{k=1}^{N}\psi(k)\psi^T(k). \tag{22}$$

Accordingly, the equation (22) is expressed as follows:

$$J_N(\theta)=c(N)+2\theta^T f(N)+\theta^T R(N)\theta. \tag{23}$$

wherein c(N), f(N) and R(N) are the following equations (24), (25) and (25), respectively:

$$R(N) = \frac{1}{N}\sum_{k=1}^{N}\psi(k)\psi^T(k): m\times m \text{ matrix } (m \text{ is a dimension of } \theta), \tag{24}$$

$$f(N) = \frac{1}{N}\sum_{k=1}^{N}y(k)\psi(k): m \text{ dimension vector}, \tag{25}$$

$$c(N) = \frac{1}{N}\sum_{k=1}^{N}y^2(K): \text{ scalar}. \tag{26}$$

Since the evaluation norm $J_N(\theta)$ is a quadric function, when a coefficient of the quadric term of the quadric function, the evaluation norm $J_N(\theta)$ takes a minimum value at a point where a derivative of $J_N(\theta)$ takes zero. When the derivative of the equation (23) is zero, the following normal equation (simultaneous linear equation) is obtained.

$$R(N)\theta(N)=f(N). \tag{27}$$

Figure 10:
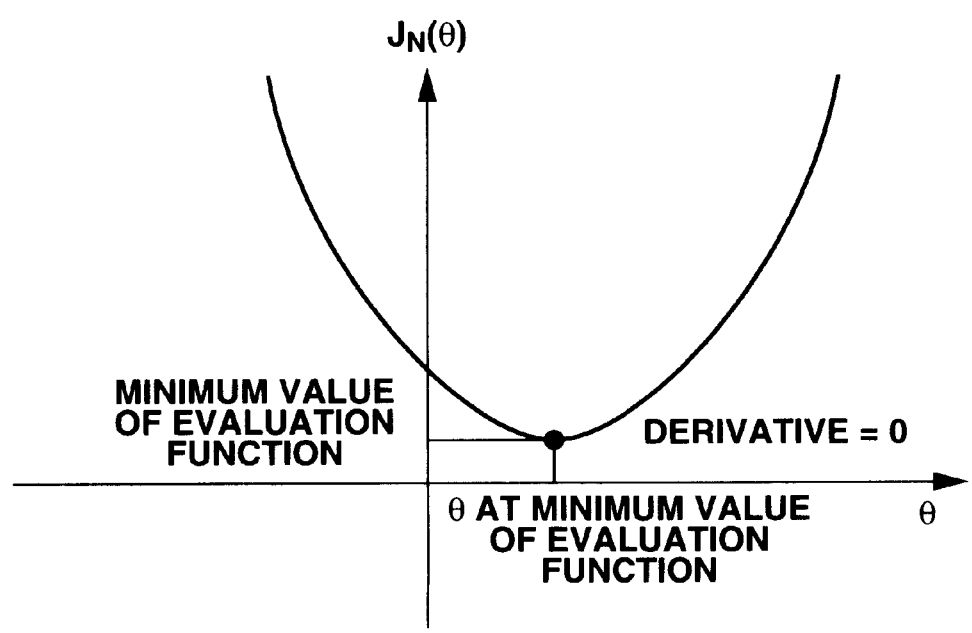
FIG. 10 is a graph showing a characteristic of an evaluation function of a norm model.

Accordingly, if R(N) is a positive definite matrix, $J_N(\theta)$ takes zero in case that the derivative of $J_N(\theta)$ takes zero. That is, $J_N(\theta)$ is a positive curvature as shown in FIG. 10. The parameter $\theta(N)$ is estimated from the following equation (28):

$$\theta(N)=R^{-1}(N)f(N). \tag{28}$$

Figure 11:
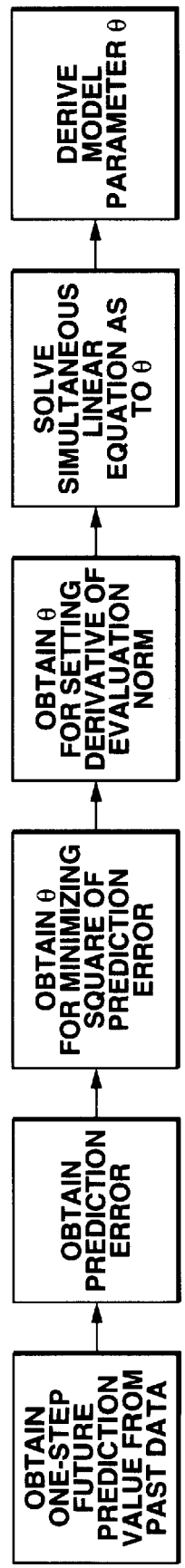
FIG. 11 is a flowchart showing an identification method of ARX model.

FIG. 11 shows the identification procedures mentioned in the above.

The following three conditions are necessary conditions of the above-mentioned positive definite matrix.

(1) When the identified object is n-degree, it is necessary that the input signal u(k) includes sine waves whose number is greater than n. That is, it is necessary that the step input signal includes a sufficient quantity of frequency components.

(2) The identified object is stable. It may be supposed that an engine operation in a stationary region is a stable system.

(3) The identified object has observability. That is, there is no common factor between $A(q,\theta)$ and $B(q,\theta)$. Since the present model is a discrete system, the degree of $B(q,\theta)$ is higher than that of $A(q,\theta)$. Therefore, this model satisfies the third condition.

2.4 Actual Identification of ARX model

The present model is a discrete system model including a third-degree denominator and a third-degree denomination as represented by the equation (7). Therefore, the present model is represented by the following equations (29) and (30):

$$A(q)=1+a_1 \cdot q^{-1}+a_2 \cdot q^{-2}+a_3 \cdot q^{-3} \tag{29}$$

$$B(q)=b_1 \cdot q^{-1}+b_2 \cdot q^{-2}+b_3 \cdot q^{-3}. \tag{30}$$

Therefore, the parameter vector $\theta$ and the data vector $\psi(k)$ are represented as follows:

$$\theta=[a_1,a_2,a_3, b_1, b_2, b_3]^T. \tag{31}$$

$$\psi(k)=[-y(k-1),-y(k-2),-y(k-3),u(k-1), -u(k-2),-u(k-3)] \tag{32}$$

When it is supposed that the total number N of samplings under a condition of the engine rotation speed of 1200 rpm, the equations (24) to (26) are represented as follows:

$$R(N) = \frac{1}{128}\sum_{k=1}^{132} \psi(k)\psi^T(k) \tag{33}$$

$$= \frac{1}{128}\left\{ \begin{bmatrix} -y(3) \\ -y(2) \\ -y(1) \\ u(3) \\ u(2) \\ u(1) \end{bmatrix} \times [-y(3) \; -y(2) \; -y(1) \; u(3) \; u(2) \; u(1)] + \right.$$

$$\begin{bmatrix} -y(4) \\ -y(3) \\ -y(2) \\ u(4) \\ u(3) \\ u(2) \end{bmatrix} \times [-y(4) \; -y(3) \; -y(2) \; u(4) \; u(3) \; u(2)] + \dots +$$

$$\left. \begin{bmatrix} -y(128) \\ -y(127) \\ -y(126) \\ u(128) \\ u(127) \\ u(126) \end{bmatrix} \times [-y(128) \; -y(127) \; -y(126) \; u(128) \; u(127) \; u(126)] \right\}$$

$$f(N) = \frac{1}{128}\sum_{k=1}^{132} y(k)\psi(k) \tag{34}$$

$$= \frac{1}{128}y(4)\times\begin{bmatrix} -y(3) \\ -y(2) \\ -y(1) \\ u(3) \\ u(2) \\ u(1) \end{bmatrix} + y(5)\times\begin{bmatrix} -y(4) \\ -y(3) \\ -y(2) \\ u(4) \\ u(3) \\ u(2) \end{bmatrix} + \dots +$$

$$y(123)\times\begin{bmatrix} -y(128) \\ -y(127) \\ -y(126) \\ u(128) \\ u(127) \\ u(126) \end{bmatrix}$$

$$c(N) = \frac{1}{128}\sum_{k=1}^{132} y^2(k) = \frac{1}{128}(y(4)^2 + y(5)^2 + \dots + y(132)^2). \tag{35}$$

2.5 Input Signal Necessary for Plant Identification

Figure 12:
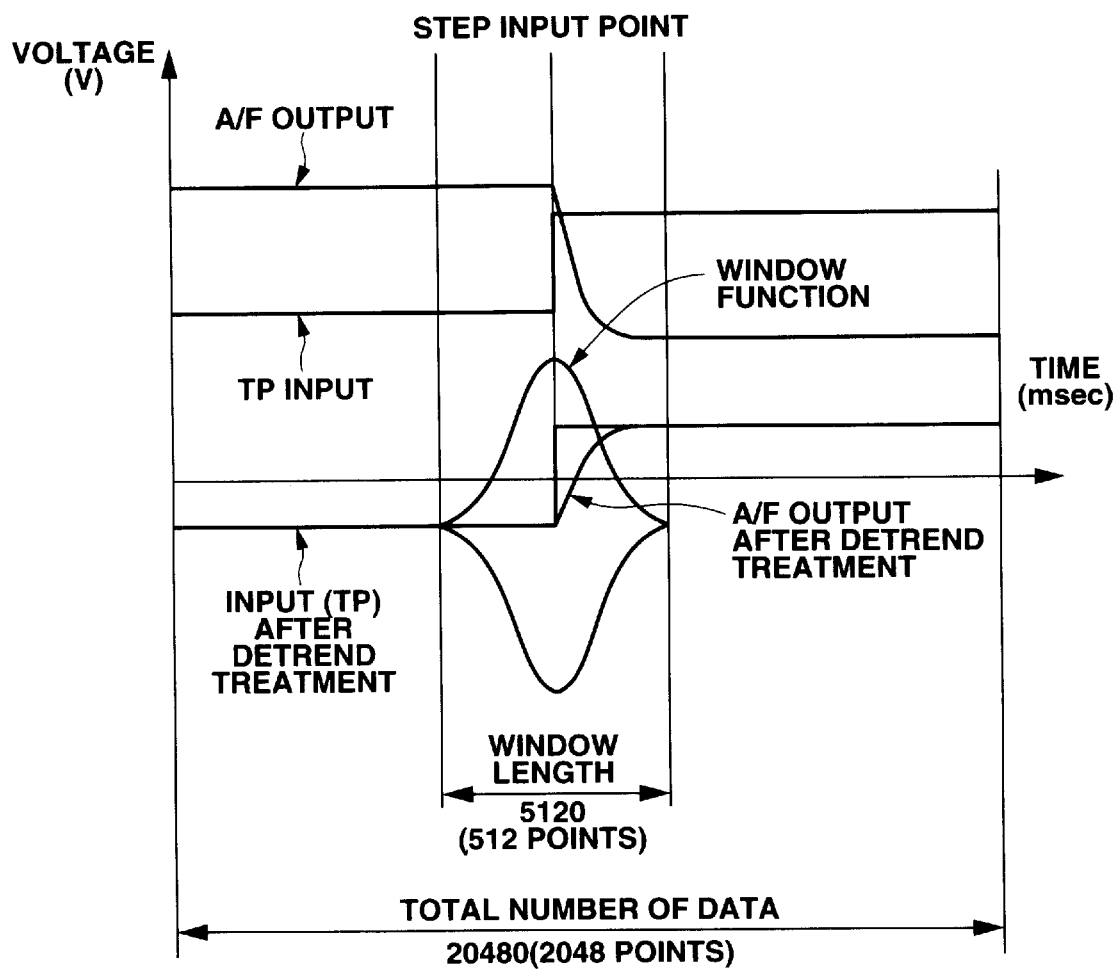
FIG. 12 is a wave-form diagram showing an input signal and a response thereof necessary for the model identification.

In order to execute the identification of the system, it is necessary that the input signal excites all modes of the object. That is, it is necessary that the input signal includes a large number of frequency components. White-like input is an ideal of an input employed in the system identification, and practically false white two-value input is employed for the system identification. However, an effective frequency band of the wall-flow response of the engine ranges in a very low frequency range, that is, the response speed is very low. Therefore, it is difficult to obtain a response wave-form in reply to the input of M time-series. Therefore, on the basis of a wave-form obtained by applying a step input as shown in FIG. 12, the system identification is executed. Since Laplace transformation of the step input is 1/s, the frequency gain is varied in inverse proportion with respect to the frequency. Therefore, it is necessary to previously determine an effective frequency band which is more effective than the power spectrum.

2.6 Result of Experiment

By employing the parameter $\theta$ obtained by the above-mentioned method, the transfer function $G(q,\theta)$ of the system is determined. Bode diagrams of FIGS. 13A to 13D show the identification results and actual data. FIGS. 13A and 13B are Bode diagrams as to light gasoline, and FIGS. 13C and 13D are Bode diagrams as to heavy gasoline. As clearly shown in these Bode diagrams, the cutoff frequency of the identified model tends to be increased according to the lightness of the fuel property. According to the experimental result, when the engine 1 is operated in a condition that the swirl control valve 51 in the intake port is open, the engine rotation speed is about 1200 rpm, the cooling water temperature is about 40° C. and the engine load is low, two kinds of gasoline, which has different fuel properties are distinguished with an accuracy of $\pm 3\sigma$.

Next, the control executed by the ECM 2 will be discussed with reference to flowcharts of FIGS. 14 to 17.

Figure 14:
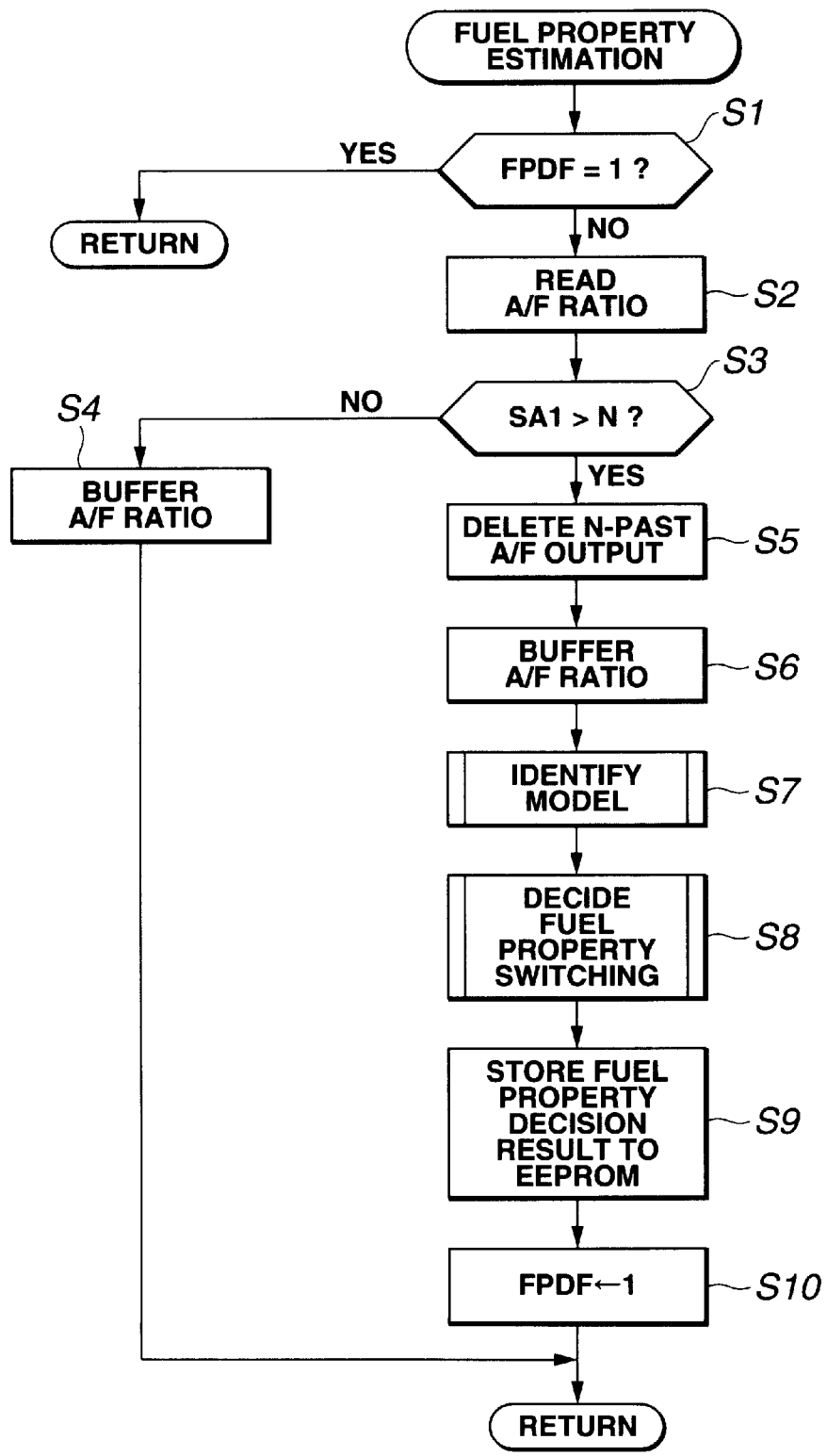
FIG. 14 is a flowchart employed for explaining the estimation of the fuel property.
Figure 15:
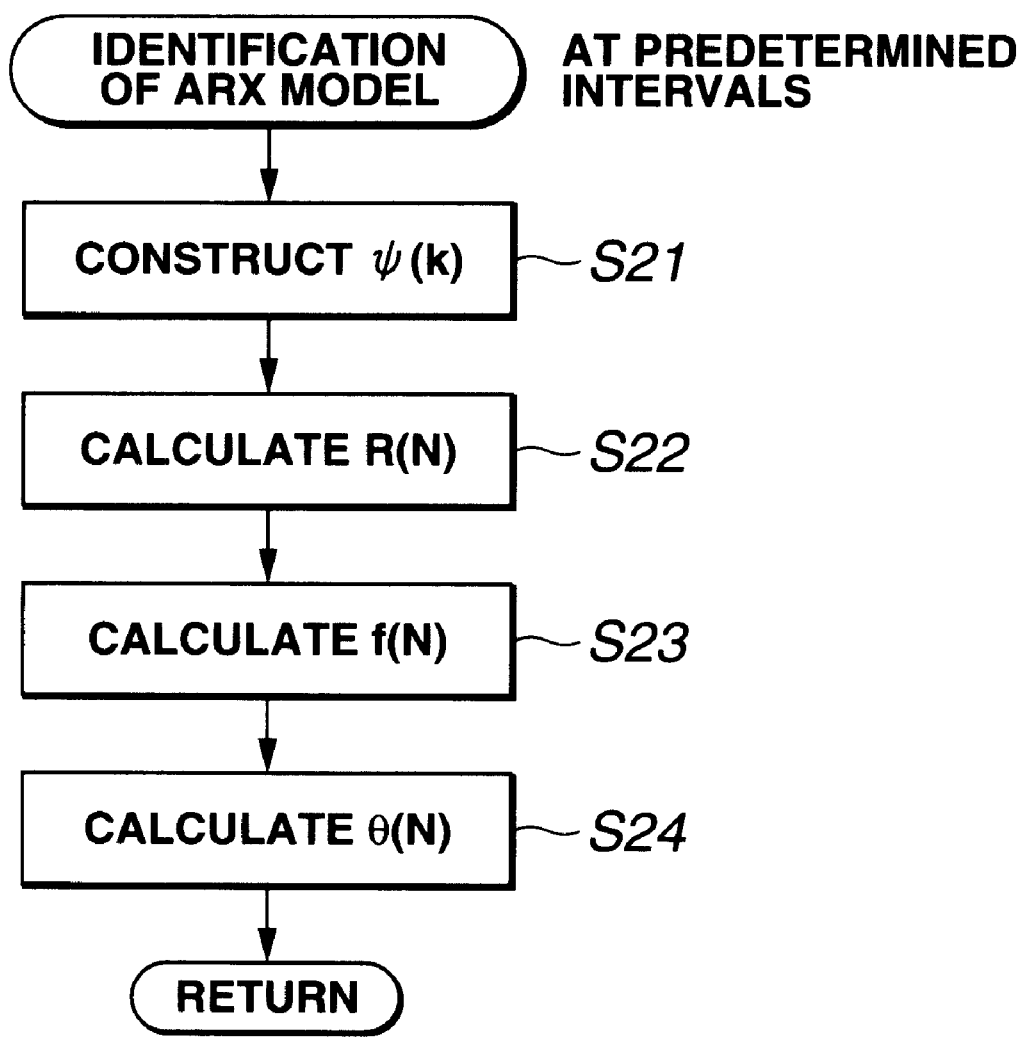
FIG. 15 is a flowchart employed for explaining the identification of ARX model.
Figure 16:
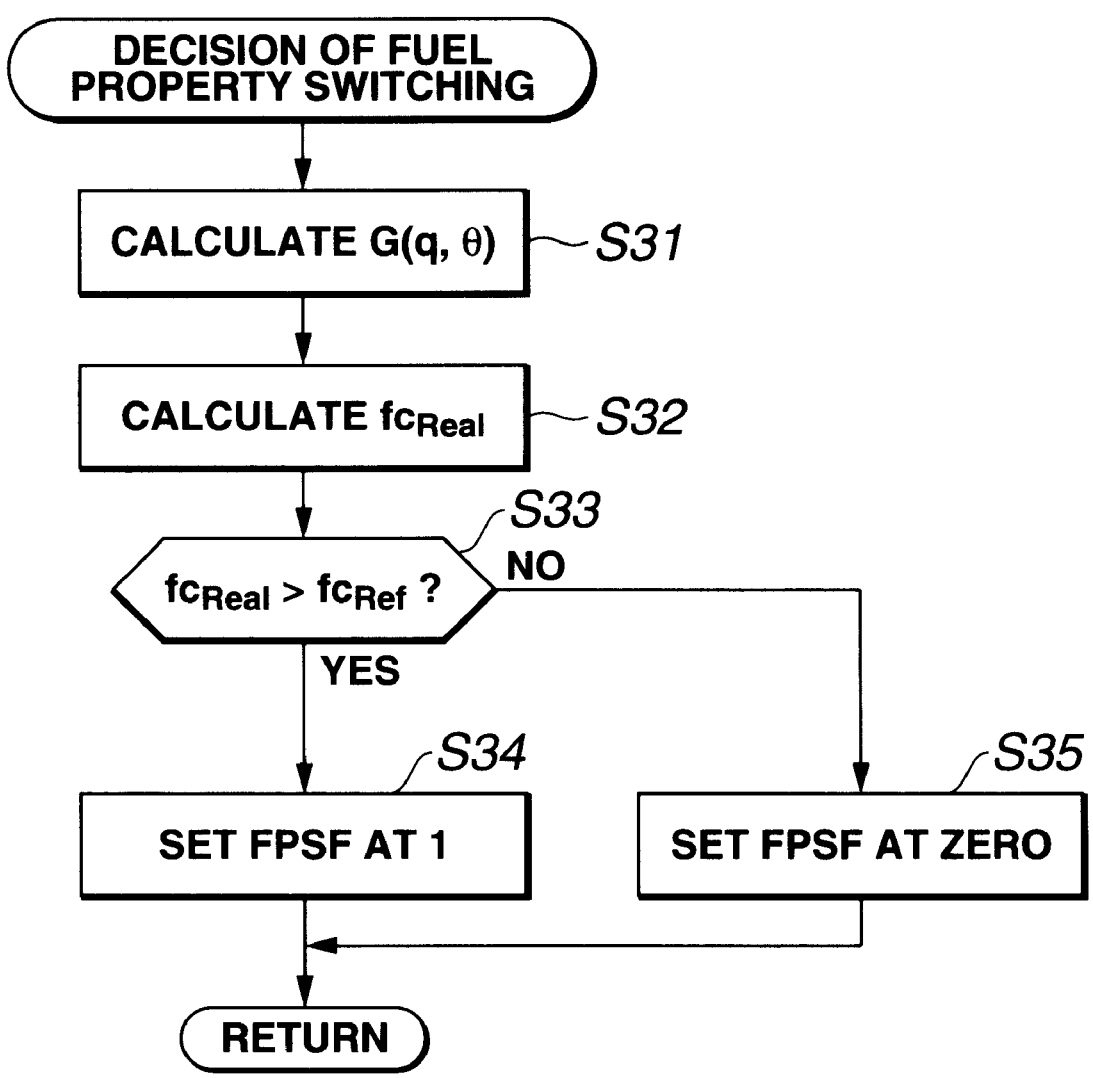
FIG. 16 is a flowchart employed for explaining the switching decision of the fuel property.

A flowchart of FIG. 14 shows a procedure for estimating the fuel property and is executed at predetermined intervals. In this first embodiment, the execution interval of this routine shown in FIG. 14 is 10 ms. The flowchart of FIG. 14 is a main routine for executing the estimation of the fuel property, and flowcharts of FIGS. 15 and 16 are subroutines executed in the main routine of FIG. 14. Therefore, the explanation of these subroutine will be given when corresponding steps to these subroutine are explained.

At a step S1, the ECM 2 checks a fuel property decision completion flag FPDF and decides whether the flag FPDF is set at 1 or not. The fuel property decision completion flag FPDF indicates whether this main routine has already executed once or more after the engine 1 is started. That is, FPDF=1 represents that a step of deciding the fuel property in this main routine has been already executed once or more in this trip. Therefore, when the decision at the step S1 is affirmative, the routine jumps to a return block to terminate the present routine. When the decision at the step S1 is negative, the routine proceeds to a step S2.

During the steps S2 to S6, the ECM 2 executes the sampling of the exhaust air/fuel ratio (output data). More specifically, at the step S2, the ECM 2 reads the air-fuel ratio detected by the A/F sensor 3. That is, the ECM 2 executes sampling of output data. At the step S3, the ECM 2 decides whether the number SA1 of samples (output data in response to input data) is greater than a predetermined number N or not. In this embodiment, the predetermined number N is set at 128. When the decision at the step S3 is negative, the routine proceeds to a step S4 wherein the ECM 2 temporally stores (buffers) the air-fuel ratio in a buffer storage and terminates the present routine. That is, until the number SA1 reaches the predetermined number N, the steps S1, S2, S3 and S4 are repeatedly executed at 10 ms intervals. When the decision at the step S3 is affirmative, that is, when SA1>N, the routine proceeds to a step S5. At this timing, the buffer storage has already stored a number N of the output data. More specifically, a present output data is stored in y(1), a previous time output data in y(2), twice past output data in y(3) - - - , N-1 times past output data in y(N).

At the step S5, the ECM 2 deletes the output data stored at N times past. At the step S6, the ECM 2 buffers the air-fuel ratio read in this routine. That is, the present output data is stored in y(N) of the buffer storage and the past data in the buffer is sequentially shifted to an older side in the buffer storage. Similarly, an actual injection pulse width (input data) CTIn at the step response is buffered in the buffer storage. More specifically, the present input data is stored in u(1), a previous time input data in u(2), twice times past input data in u(3), - - - , N-1 times past input data in u(N). Accordingly, these input data are corresponded to the output data upon taking account of the delay time.

At steps S7 and S8, the ECM 2 executes the analysis of the response wave-form of the exhaust air-fuel ratio at a time the actual injection pulse width is varied from the input and output data stored in the buffer storage. Further, on the basis of this analysis result, the ECM 2 estimates the fuel property of the employed fuel (fuel in use).

The meaning of "the analysis as to the response wave-from of the exhaust air-fuel ratio" is to identify ARX model by controlling the parameter θ of the ARX model on the basis of the input and output data so as to minimize the prediction error of the ARX model with respect to the norm model. This identification procedure of the ARX model will be discussed with reference to the flowchart of FIG. 15. Further, the estimation of the fuel property will be discussed with reference to the flowchart of FIG. 16.

As to the flowchart of FIG. 15, at a step S21 the ECM 2 constructs the data vector $\psi(k)$ from the input and output data stored in the buffer storage and the equation (32). The input data is stored in u(1) to u(128) of the buffer storage, and the output data are stored in –y(1) to –y(128).

At a step S22, the ECM 2 calculates R(N) from the data vector $\psi(k)$ and the equation (33). At a step S23, the ECM 2 calculates f(N) from the output data y(k), the data vector $\psi(k)$ and the equation (34). Further, at a step S24, the ECM 2 calculates the model parameter θ from R(N), f(N) and the equation (28).

Next, the subroutine shown in FIG. 15 is terminated, and the routine returns to a step S8. The execution of the step S8 is the decision as to whether the fuel property is switched or not, and is achieved by executing the subroutine of FIG. 16.

At a step S31, the ECM 2 calculates the transfer function $G(q,\theta)$ of the discrete time series LTI system. More specifically, the ECM 2 constructs A(q) and B(q) from θ and the equations (29) and (30) and calculates the $G(q,\theta)$ from the prepared A(q) and B(q) and the equation (8).

At a step S32, the ECM 2 calculates the cutoff frequency $fc_{Real}$ of the ARX model from the system transfer function $G(q,\theta)$.

At a step S33, the ECM 2 compares the cutoff frequency $fc_{Real}$ of the ARX model with the cutoff frequency $fc_{Ref}$ of the norm model. More specifically, the ECM 2 decides whether or not the cutoff frequency $fc_{Real}$ of the ARX model is greater than the cutoff frequency $fC_{Ref}$ of the norm model. In this embodiment heavy gasoline is employed as reference fuel. Therefore, if light gasoline is practically used during this trip, the cutoff frequency $fc_{Real}$ of the ARX model becomes greater than the cutoff frequency $fc_{Ref}$ of the norm model ($fc_{Real} > fc_{Ref}$). Further if heavy gasoline is practically used, the cutoff frequency $fc_{Real}$ of the ARX model becomes smaller than or euqal to the cutoff frequency $fc_{Ref}$ of the norm model ($fc_{Real} < fc_{Ref}$). Accordingly, when $fc_{Real} > fc_{Ref}$, that is, when light gasoline is practically used, the routine proceeds to a step S34 wherein the fuel property switching flag FPSF is set at 1 (FPSF=1). When $fc_{Real} < fc_{Ref}$, that is, when heavy gasoline is practically used, the routine proceeds to a step S33 wherein the fuel property switching flag FPSF is set at 0 (FPSF=0).

After the execution of the step S34 or S35, the routine returns to the step S9 of the main routine of FIG. 14. At the step S9, the ECM 2 stores the content of the fuel property switching flag FPSF indicative of the decision result in the EEPROM 14.

At a step S10, the ECM 2 sets the fuel property decision completion flag FPDF at 1 (FPDF=1). By this setting of FPDF=1, the routine in this program cannot proceed to the step S2 as far as this main routine is repeated without resetting the flag FPDF. That is, the decision of the fuel property is executed once a trip (from engine start to engine stop).

By enabling the decision of the fuel property practically used in the vehicle VE, it becomes possible to set various correction quantities of the fuel injection quantity and a start fuel injection quantity according to the property of the used fuel.

Figure 17:
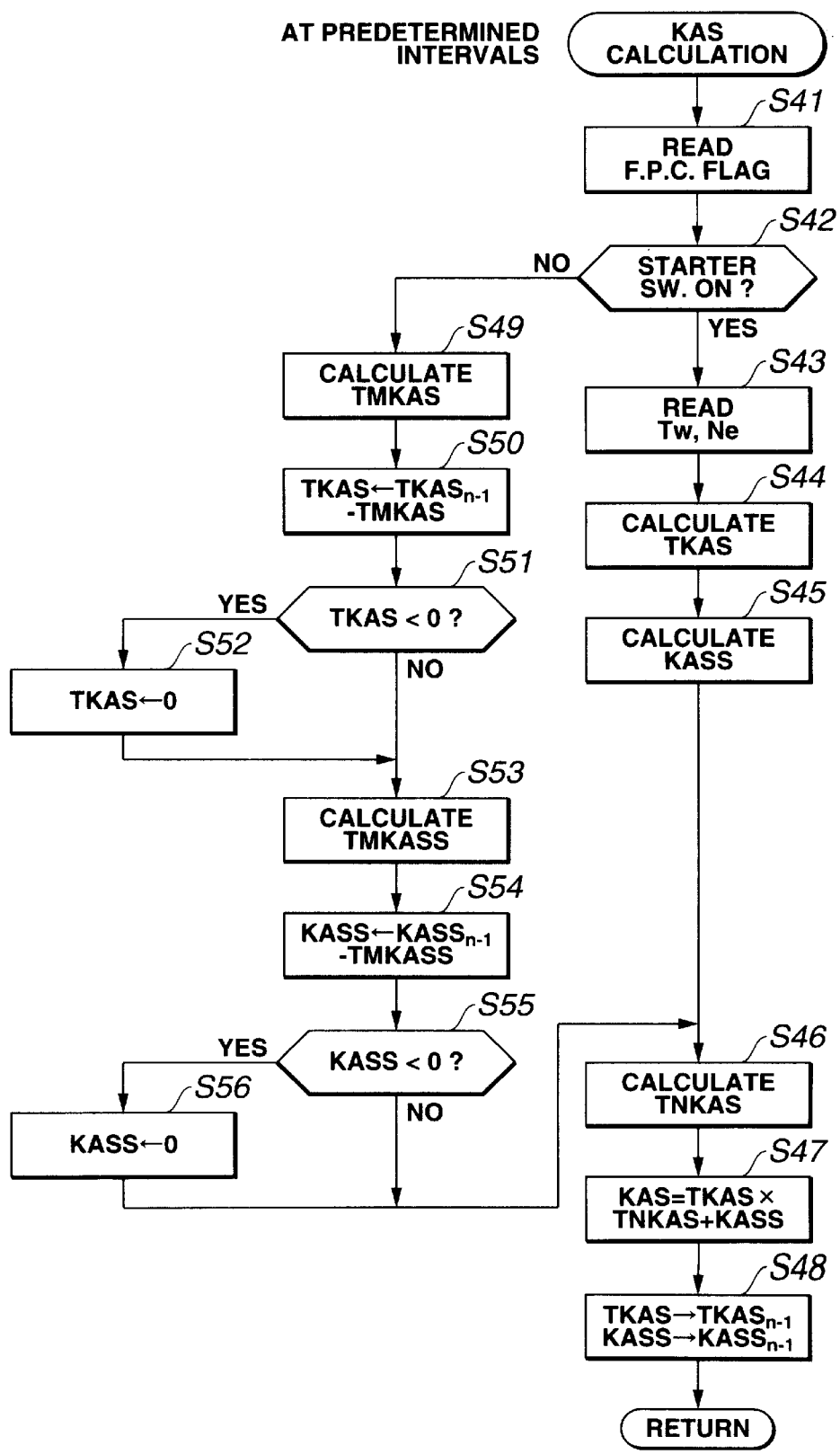
FIG. 17 is a flowchart employed for explaining the calculation of a post-start increase correction coefficient KAS.

As to the post-start increase correction coefficient KAS, a calculation process thereof will be discussed with reference to FIG. 17 in detail. This routine is executed at 10 ms intervals.

At a step S41, the ECM 2 reads the fuel property switching flag FPSF.

At a step S42, the ECM 2 checks ON-OFF state of the starter switch of the engine 1. When the starter switch is set at ON state, the routine proceeds to a step S43 wherein the ECM 2 reads the cooling water temperature Tw and the engine rotation speed Ne. When the starter switch is set at OFF state, the routine proceeds to a step S49.

Figure 18:
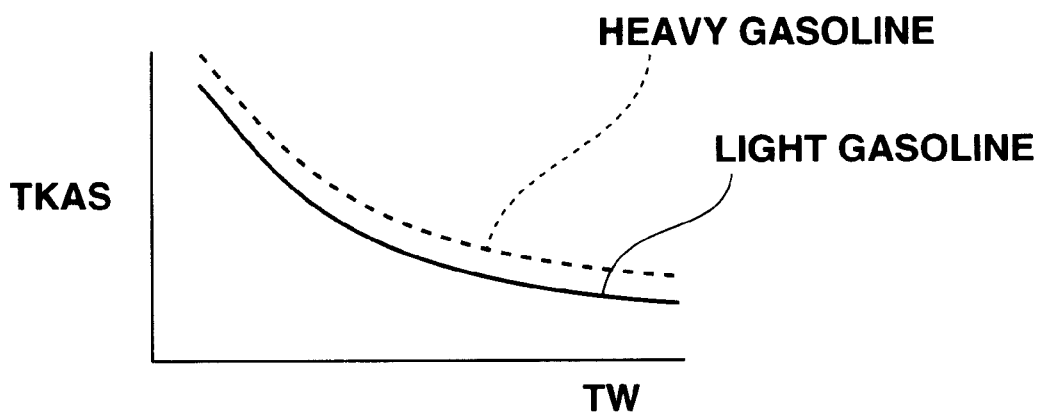
FIG. 18 is a characteristic view of a post-start increase water temperature correction value.

At a step S44 following to the step S43, the ECM 2 calculates a post-start increase water temperature correction value TKAS by retrieving a table corresponding to a graph shown in FIG. 18 on the basis of the cooling water temperature Tw and the content of the fuel property switching flag FPSF.

Figure 19:
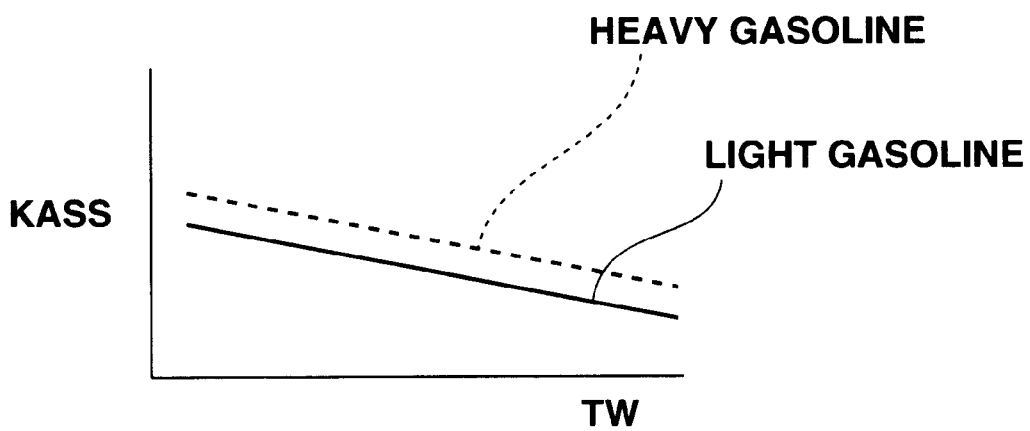
FIG. 19 is a characteristic view of a second post-start increase correction coefficient.

Similarly, at a step S45, the ECM 2 calculates a second post-start increase water temperature correction value KASS by retrieving a table corresponding to a graph shown in FIG. 19 on the basis of the cooling water temperature Tw and the content of the fuel property switching flag FPSF.

Figure 20:
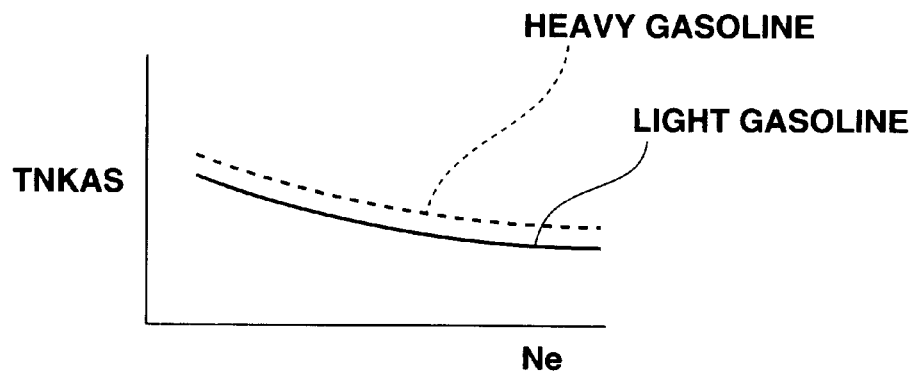
FIG. 20 is a characteristic view of a post-start increase rotation-speed correction value.

At a step S46, the ECM 2 calculates a post-start increase rotation correction value TNKAS by retrieving a table corresponding to a graph shown in FIG. 20 on the basis of the engine rotation speed Ne and the content of the fuel property switching flag FPSF.

At a step S47, the ECM 2 calculates the post-start increase correction coefficient KAS from the calculated correction values TKAS, KASS and TNKAS and the following equation:

$$KAS = TKAS \times TNKAS + KASS. \tag{36}$$

At a step S48, the ECM 2 stores the calculated correction values TKAS and KASS in addressed portions $TKAS_{n-1}$ and $KASS_{n-1}$ of the EEPROM so that the ECM 2 correctly operates even if the starter switch is turned OFF.

In the next routine, the starter switch is turned OFF, that is, the engine 1 has been started, and therefore the routine proceeds from the step S42 to a step S49 to execute an attenuating operation.

Figure 21:
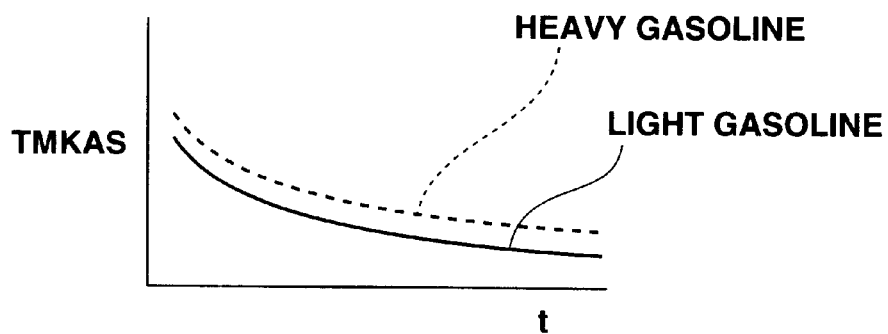
FIG. 21 is a characteristic view of a post-start increase decreasing time rate.

At the step S49, the ECM 2 calculates a post-start increase decreasing time rate TMKAS by retrieving a table corresponding to a graph shown in FIG. 21 on the basis of the content of the fuel property switching flag FPSF and an elapsed time t from the start of the engine 1.

As a step S50, the ECM 2 calculates the present-time post-start increase water temperature correction value TKAS by subtracting the calculated TMKAS from the previous-time post-start increase water temperature correction value $TKAS_{n-1}$ ($TKAS \leftarrow TKS_{n-1}-TMKAS$).

At a step S51, the ECM 2 decides whether TKAS<0 or not. When the decision at the step S51 affirmative, the routine proceeds to a step S52 wherein the post-start increase water temperature correction value TKAS is set at zero (TKAS←0). When the decision at the step S51 is negative, the routine proceeds to a step S53. At a time just after the starter switch was turned off, TKAS>0. Therefore, at that time the routine proceeds to the step S53.

Figure 22:
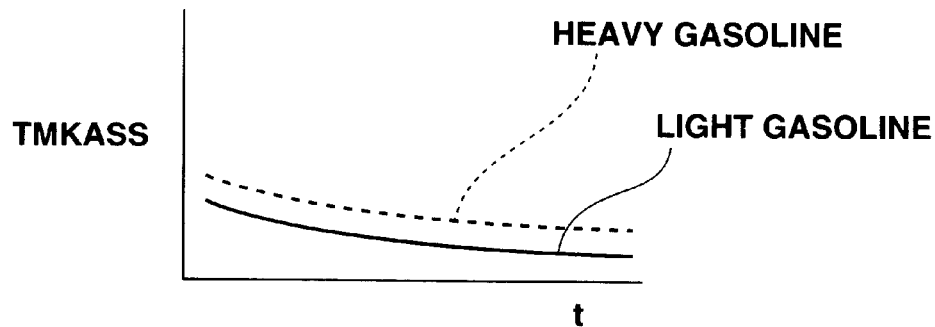
FIG. 22 is a characteristic view of a second post-start increase decreasing time rate.

At the step S53, the ECM 2 calculates a second post-start increase decreasing time rate TMKASS by retrieving a table corresponding to a graph shown in FIG. 22 on the basis of the content of the fuel property switching flag FPSF and an elapsed time t from the start of the engine 1.

As a step S54, the ECM 2 calculates a present-time second post-start increase correction value KASS by subtracting the calculated TMKASS from the previous-time second post-start increase correction value $KASS_{n-1}$ ($KASS \leftarrow KASS_{n-1}-TMKASS$).

At a step S55, the ECM 2 decides whether KASS<0 or not. When the decision at the step S55 affirmative, the routine proceeds to a step S56 wherein KASS is set at zero (KASS←0) and then proceeds to the step S46. When the decision at the step S56 is negative, the routine proceeds to a step S46. Since at the first-time routine after the negative-decision at the step S42 KASS>0, this routine proceeds to the step S46.

Further, in the following next-time routine, the execution of the step S49, S50, S53 and S54 are repeated, and at last the values TKAS and KASS take values smaller that zero. In such a condition, the steps S52 and S56 are respectively executed so as to set the values TKAS and KASS at zero, respectively. Consequently, TKAS and KASS are gradually decreased from initial values taken at the time of the turn-off of the starter switch to zero by a predetermined rate, wherein TNKAS is constant. Further, the initial value TKAS is greater than that of KASS, and the decrease time rate of TKAS is greater than that of KASS. Therefore, KAS, which is the sum of TKAS and KASS, is radically deceased from an initial value, which is the sum of the initial values of TKAS and KASS at the turn-off timing of the starter switch, at high rate. Further, after a timing that TKAS reaches zero, KAS is slowly decreased at low rate.

Figure 23:
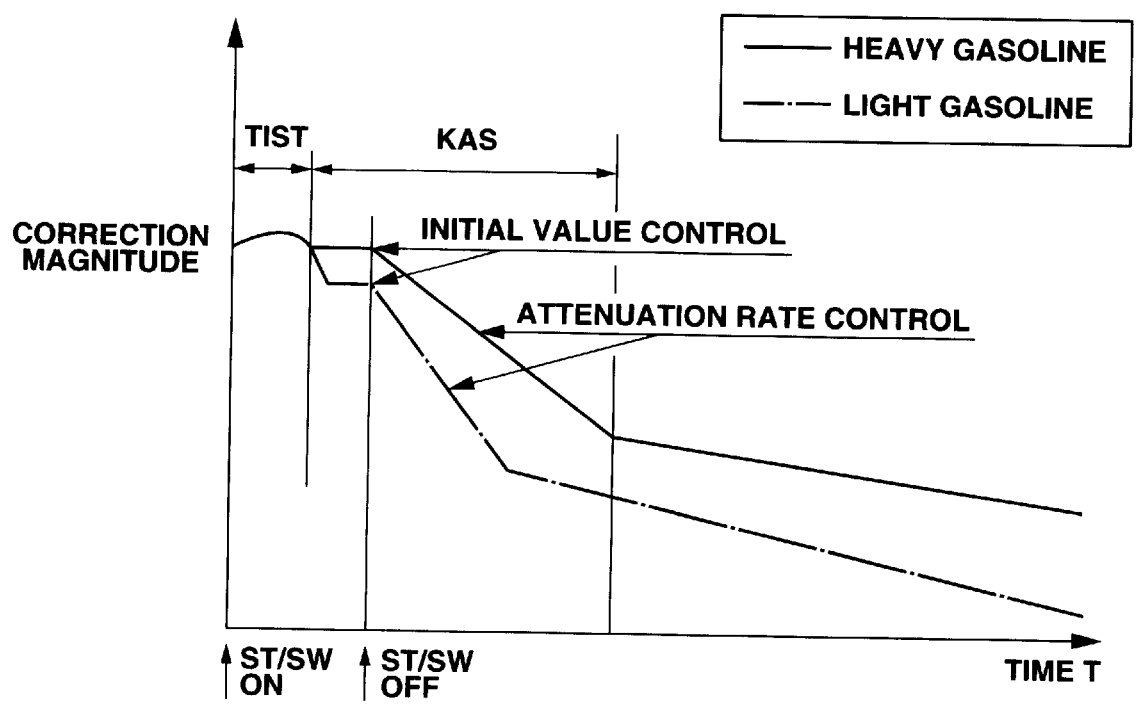
FIG. 23 is a wave-form diagram showing a time-series image of the post-start increase correction coefficient.

In this case, the initial values of TKAS and KASS are set so that those in use of light gasoline are smaller than those in used of heavy gasoline as shown in FIGS. 18 and 19. Further, the decrease time rates of TKAS and KASS are set so that those of light gasoline are smaller than those of heavy gasoline as shown in FIGS. 21 and 22. Accordingly, KAS in case of light gasoline is smaller than that in case of heavy gasoline, as shown in FIG. 23.

That is, if the decision of the fuel property is not executed and if light gasoline is used, table value of the various correction values matched with heavy gasoline are used for determining the post-start increase correction coefficient KAS. Therefore, in such a case, the air-fuel ratio becomes rich. In contrast to this, when the decision of the fuel property of employed gasoline is executed, that is, when it is decided that light gasoline is practically used in this system, KAS for light gasoline is calculated in the next start of the engine. Accordingly, even when the light gasoline is practically used in the engine 1, the air-fuel ratio is kept at a suitable ratio without shifting to the rich side.

Figure 24:
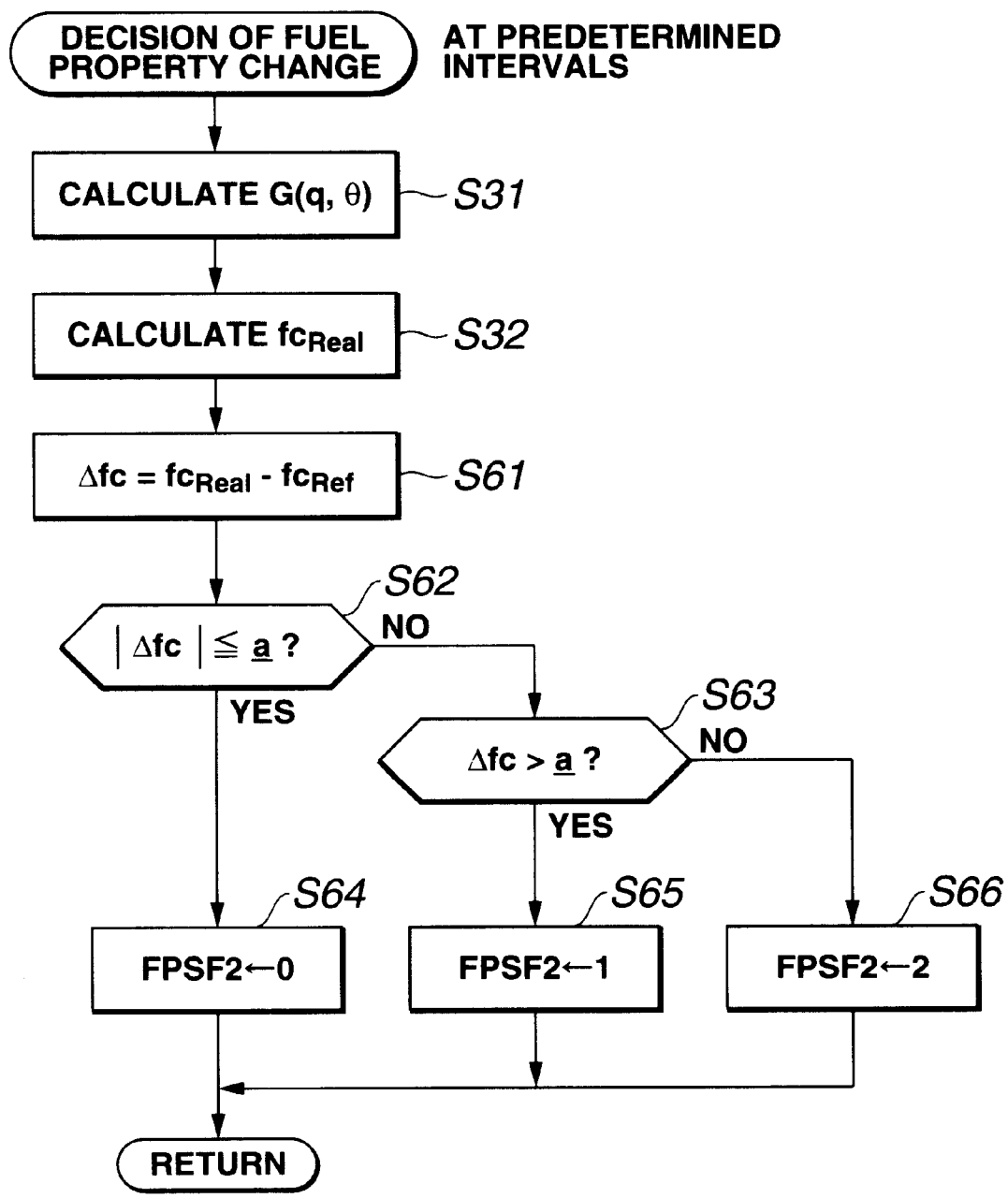
FIG. 24 is a flowchart employed for explaining a switching decision of the fuel property of a second embodiment.

Referring to a flowchart of FIG. 24, a second embodiment of the fuel property detecting system will be discussed. Basic construction of the second embodiment is as same as that of the first embodiment as shown in FIG. 1. Further, the routine for the fuel property estimation of the second embodiment employs the routine shown by a flowchart of FIG. 14 of the first embodiment. The flowchart of FIG. 24 shows the fuel property switching decision procedure corresponding to that shown in FIG. 16 of the first embodiment. In the flowchart of FIG. 24, steps as same as those of the first embodiment are denoted by same step reference numerals. The explanation of the contents as to parts and flowcharts as same as those of the first embodiment is omitted herein.

That is, the second embodiment is arranged to employ intermediate fuel having an intermediate volatility as a reference fuel, in contrast to the first embodiment in which heavy fuel having a low volatility is employed. Further, in this second embodiment, gasoline having a higher volatility with respect to the reference fuel is defined as light gasoline, and gasoline having a lower volatility with respect to the reference fuel is defined as heavy gasoline. In the procedure for deciding the fuel property, a difference between the cutoff frequency of the plant model and the cutoff frequency of the norm model is calculated, and the fuel property of the practically used gasoline is decided by comparing the difference between the cutoff frequencies and a tolerance thereof. By providing the tolerance, even if the cutoff frequency of the fuel to be decided is dispersed with respect to that of the reference fuel, it becomes possible to decide the fuel property of the practically used fuel.

The flowchart of FIG. 24 includes steps S61 to S66 instead of the step S33 to S35 employed in the flowchart of FIG. 16. Accordingly, after the execution of the step S31 and S32 for calculating $G(q,\theta)$ and $fc_{Real}$, the step S61 is executed.

At the step S61, the ECM 2 calculates a cutoff frequency difference $\Delta fc$ between the cutoff frequency of the plant model and the cutoff frequency of the norm model by employing the following equation (37):

$$\Delta fc = fc_{Real} - fc_{Ref} \tag{37}$$

At the step S62, the ECM 2 decides whether or not an absolute value of the frequency difference Δfc is smaller than or equal to a predetermined value a for defining a tolerance (allowable range) of the reference fuel. When the frequency difference Δfc is smaller than or equal to a ($|\Delta fc| \leq \underline{a}$), that is, when the used fuel corresponds to the reference fuel, the routine proceeds to a step S64 wherein the ECM 2 sets a fuel property switching flag FPSF2 at zero (FPSF2←0). When the frequency difference Δfc is greater than a ($|\Delta fc| > \underline{a}$), that is, when the used fuel is heavy fuel or light fuel, the routine proceeds to a step S63.

At the step S63, the ECM 2 decides whether or not the frequency difference Δfc is greater than the predetermined value a. When the decision at the step S63 is affirmative ($\Delta fc > \underline{a}$), that is, when light gasoline is practically used, the routine proceeds to a step S65 wherein the ECM 2 sets the fuel property switching flag FPSF2 at 1 (FPSF2←1). When the decision at the step S63 is negative ($\Delta fc < \underline{a}$), that is, when heavy gasoline is practically used, the routine proceeds to a step S66 wherein the ECM 2 sets the fuel property switching flag FPSF2 at 2 (FPSF2←2).

By executing the above-mentioned program of the second embodiment, it becomes possible to decide which of reference fuel, light fuel or heavy fuel is being used in the vehicle VE. Of coarse, it is necessary to previously provide table values necessary for calculating the post-start increase correction coefficient KAS by each of the three kinds of fuels in correspond to graphs of FIGS. 18 to 22.

Figure 25:
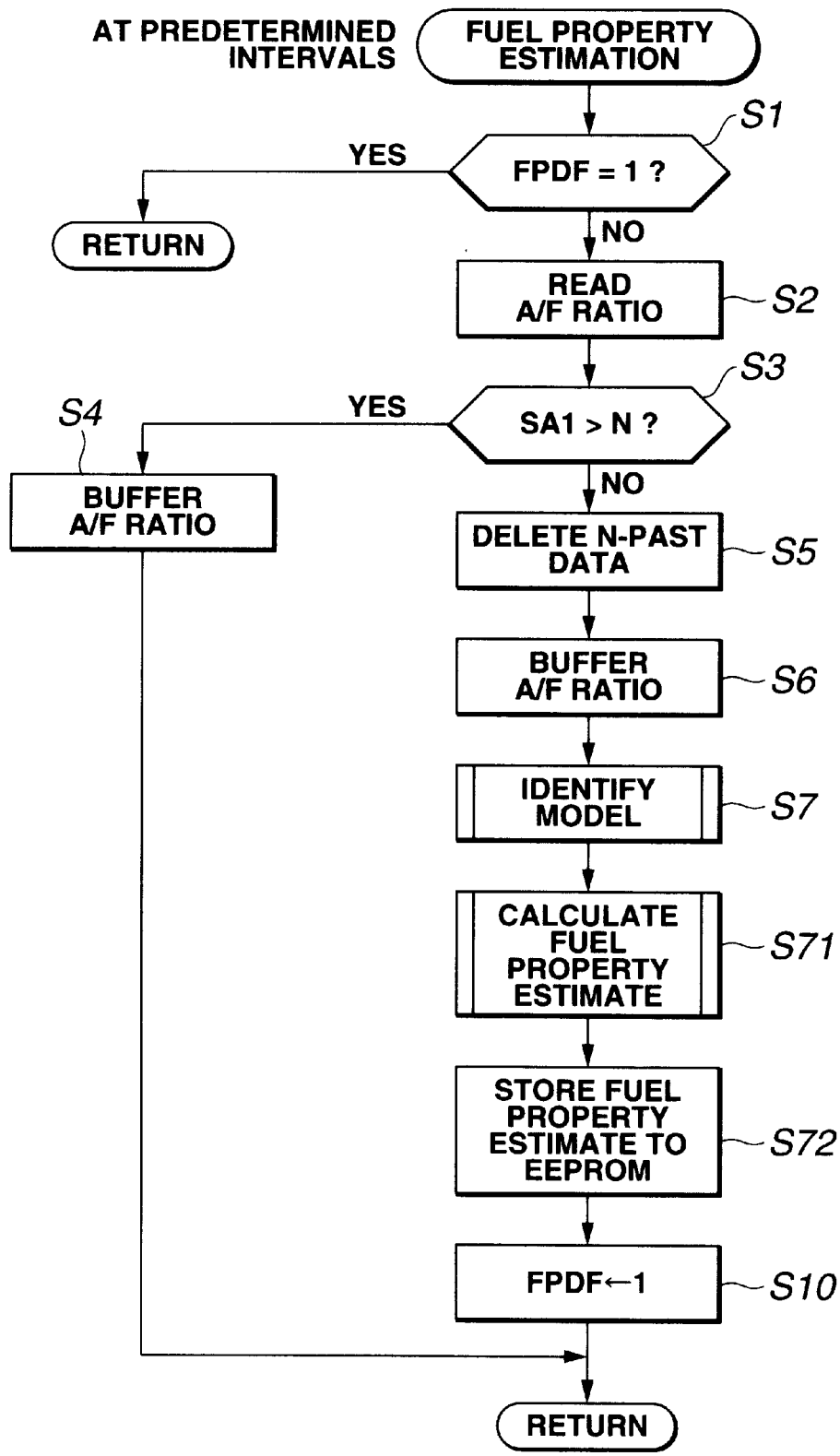
FIG. 25 is a flowchart employed for explaining the estimation of the fuel property of a third embodiment.
Figure 26:
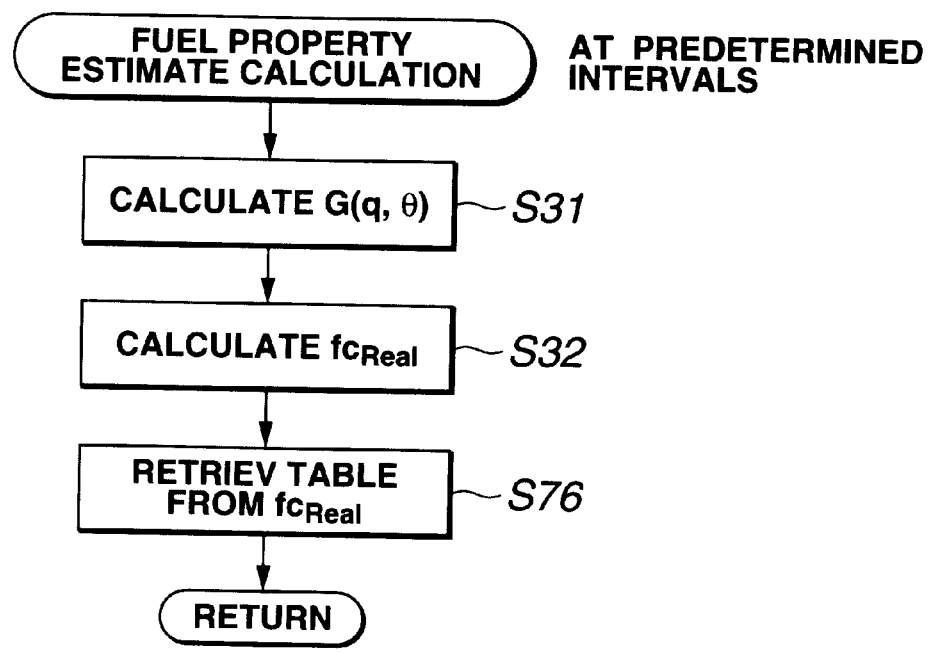
FIG. 26 is a flowchart employed for explaining the calculation of a fuel property estimate of the third embodiment.
Figure 27:
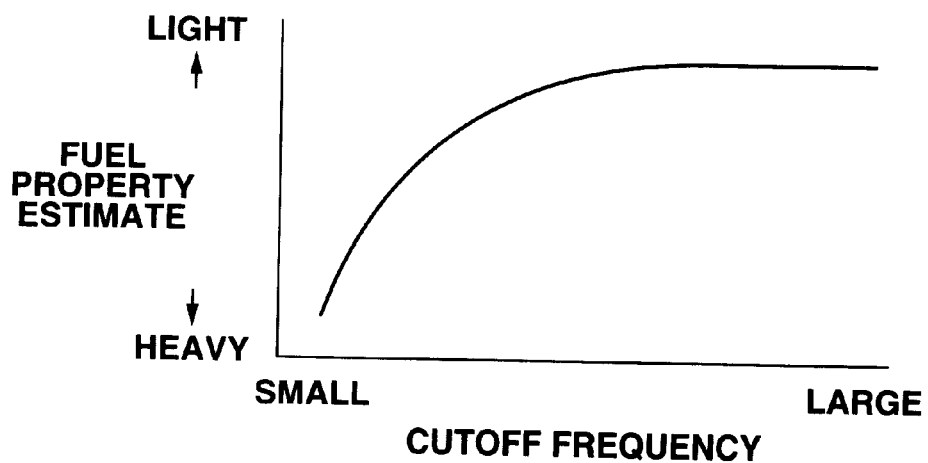
FIG. 27 is a characteristic curve showing the fuel property estimate with respect to a cutoff frequency.

Referring to FIGS. 25 to 27, a third embodiment of the fuel property detecting system will be discussed. Basic construction of the third embodiment is as same as that of the first embodiment as shown in FIG. 1, and therefore the explanation of the contents as same as those of the first embodiment is omitted herein.

The flowcharts of FIGS. 25 and 26 show the fuel property estimation procedure and the fuel property switching decision procedure corresponding to those of FIGS. 14 and 16 in the first embodiment. In the flowchart of FIG. 25, steps as same as those of FIG. 14 in the first embodiment are denoted by same step reference numerals. Further, in the flowchart of FIG. 26, steps as same as those of FIG. 16 in the first embodiment are denoted by same step reference numerals.

As is clear from the comparison between the flowchart of FIG. 25 of the third embodiment and that of FIG. 14 of the first embodiment, the flowchart of FIG. 25 of the third embodiment is arranged such that steps S71 and S72 are newly added following to the step S7. That is, the third embodiment is arranged so that the ECM 2 calculates the fuel property estimate and stores it in the EEPROM as shown in the steps S71 and S72 of the flowchart of FIG. 25. The employment of the fuel property estimate improves the calculation accuracy of the various correction quantities relating the fuel injection quantity.

As to the calculation of the fuel property estimate executed at the step S71 of the flowchart of FIG. 25, the explanation will be done with reference to the flowchart of FIG. 26 indicating the subroutine started at the step S71.

At a step S31, the ECM 2 calculates G(q,θ). At the step S32, the ECM 2 calculates the cutoff frequency $fc_{Real}$ of the plant model.

At a step S76 following to the step S32, the ECM 2 calculates the fuel property estimate by retrieving a table corresponding to a graph shown in FIG. 27 from the calculated cutoff frequency $fc_{Real}$ of the plant model. The relationship between the cutoff frequency $fc_{Real}$ of the plant model and the fuel property estimate has been obtained previously and stored in the memory of the ECM 2 in the form of the table corresponding to the graph of FIG. 27. Therefore, the third embodiment enables the fuel property of the employed fuel (fuel in use) to be estimated from the cutoff frequency of the plant model.

Figure 28:
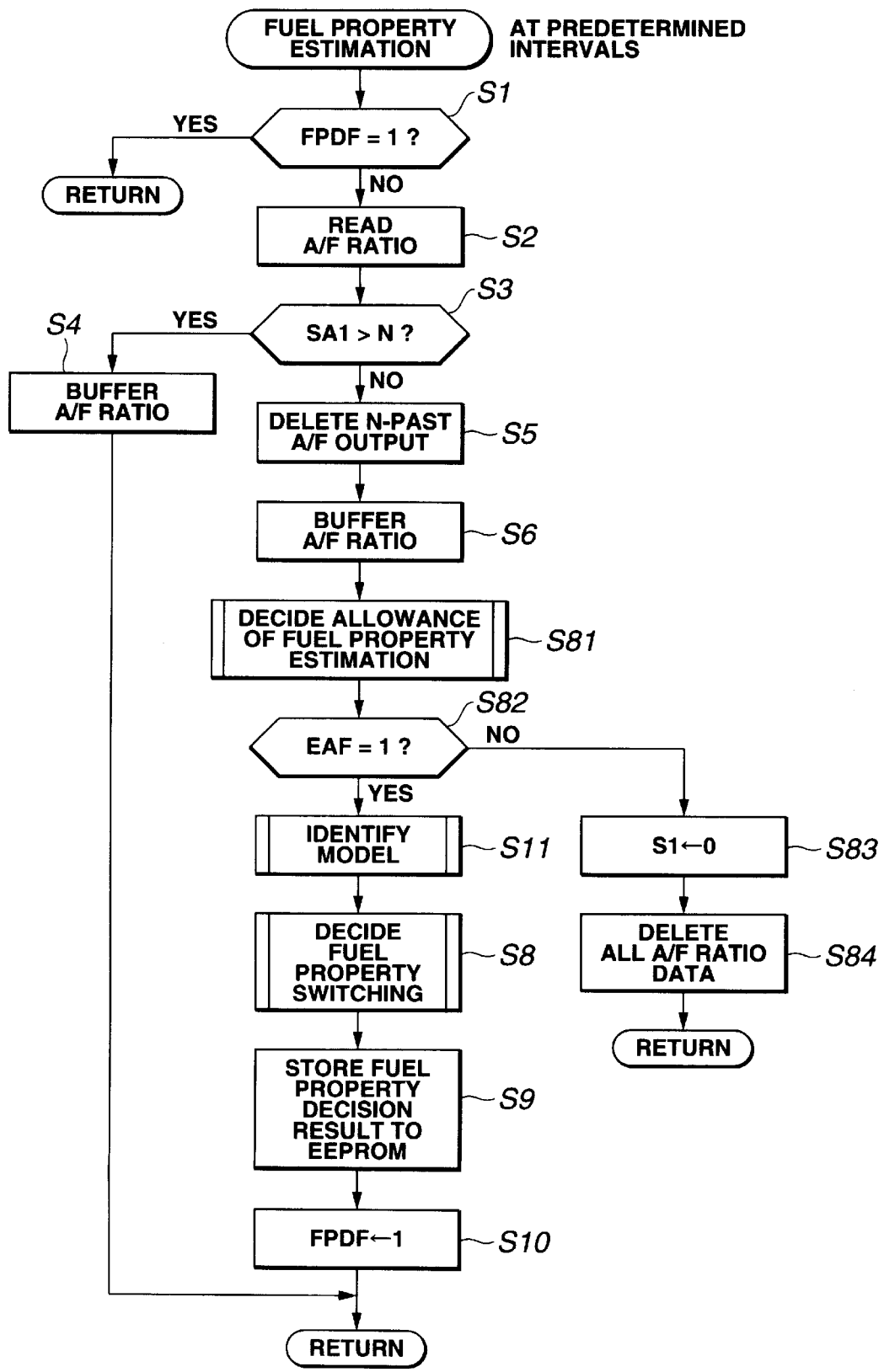
FIG. 28 is a flowchart employed for explaining the estimation of the fuel property in a fourth embodiment.
Figure 29:
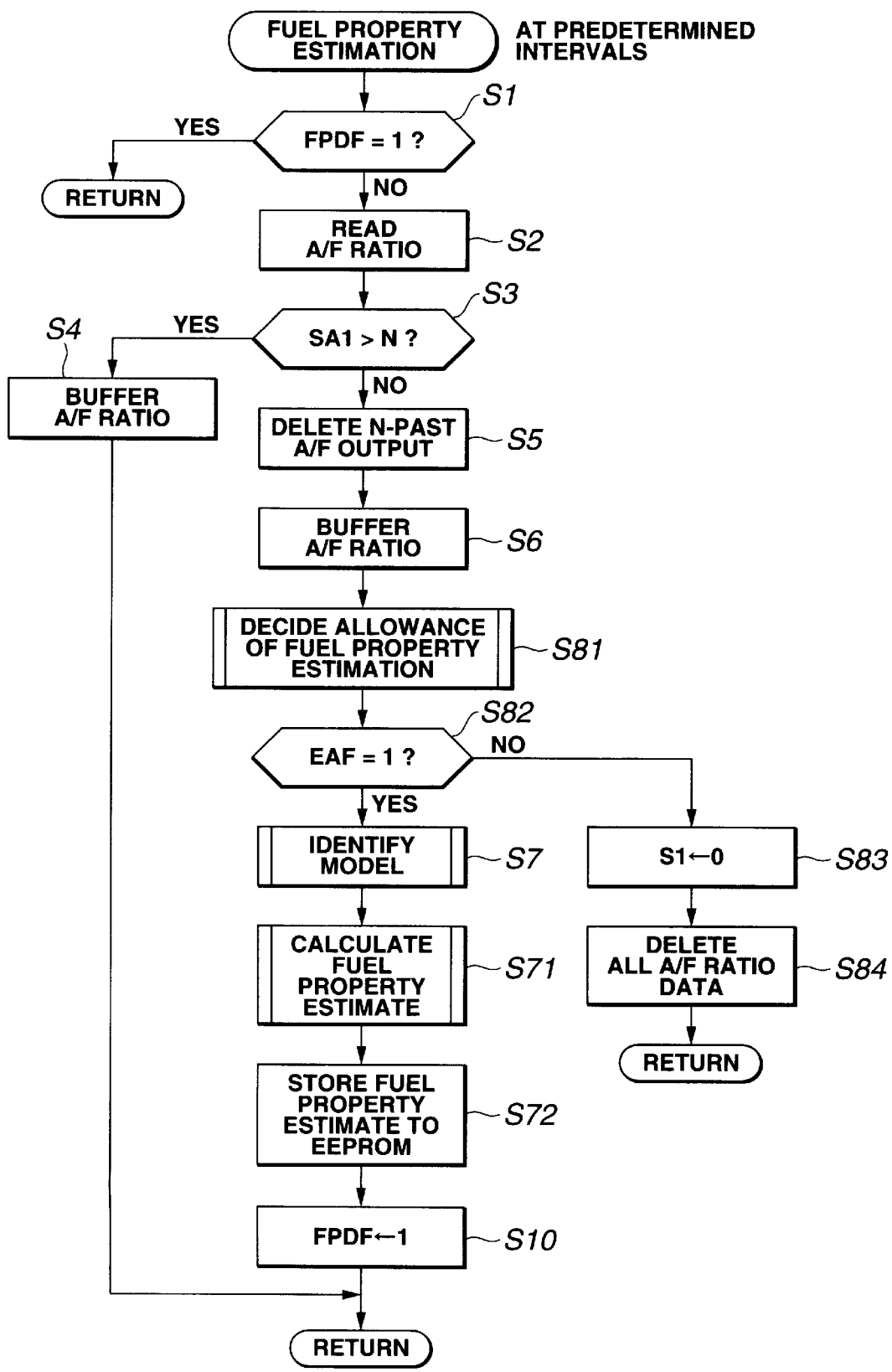
FIG. 29 is a flowchart employed for explaining the estimation of the fuel property of the fifth embodiment.
Figure 42:
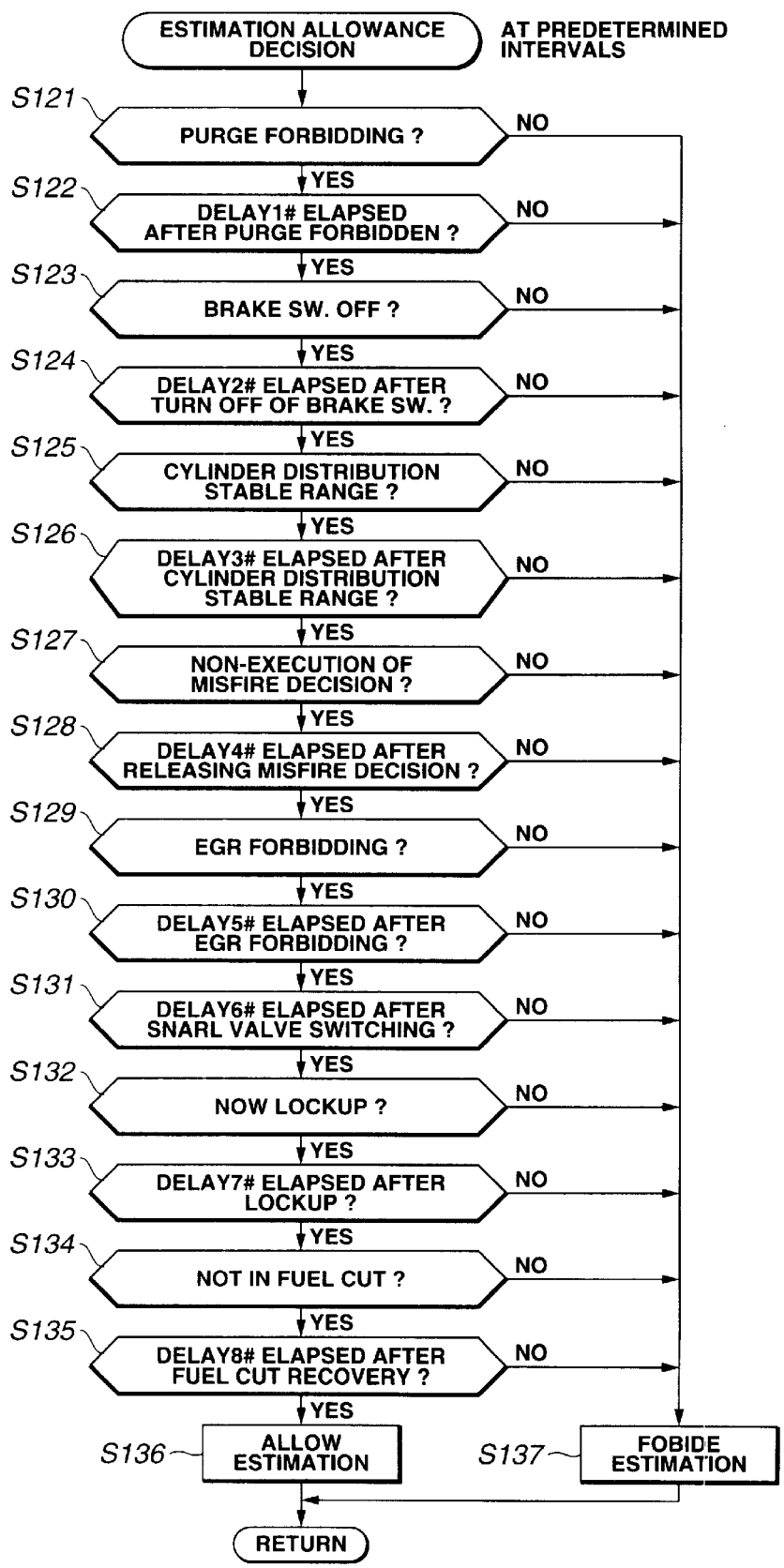
FIG. 42 is a flowchart employed for explaining an allowance decision of the execution of the fuel property estimation.

Referring to FIGS. 28 and 42, a fourth embodiment of the fuel property detecting system will be discussed. The fourth embodiment is basically constructed by elements as same as those of the first embodiment shown in FIG. 1. The fuel property estimation procedure of the fourth embodiment shown in the flowchart of FIG. 28 is generally similar to that of the first embodiment shown in FIG. 14 except that steps S81, S82, S83 and S84 are further added. Since the steps represented by same reference numerals have the same contents as those in the first embodiment, the explanation thereof is omitted herein. Only the explanation as to the newly added steps in the fourth embodiment will be made hereinafter.

At a step S81 following to the step S6 in the flowchart of FIG. 28, the ECM 2 decides whether the estimation of the fuel property may be executed or not. Detailed procedure of this decision is shown in the flowchart of FIG. 42. That is, the decision at the step S811 is executed by checking the contents of steps S121 to S135 step by step, and only when all decisions as to the contents of the steps S121 to S135 are affirmative, the estimation of the fuel property is allowed. If at least one of the decisions of the steps S121 to S135 is negative, the estimation of the fuel property is forbidden. The contents to be checked in the decision block will be discussed. More specifically, it is checked whether the following conditions (A) to (H) are satisfied or not.

A) Purging operation of the evaporative emission control system 54 is now being forbidden, and a delay time DELAY1# has elapsed from the forbidding of the purging operation. These contents are checked at the steps S121 and S122.

B) A brake switch of the brake control system 56 is set at OFF state, and a delay time DELAY2# has elapsed from the turn-off of the brake switch. These contents are checked at the steps S123 and S124.

C) The engine 1 is operating in a cylinder distribution stable region, and a delay time DELAY3# has elapsed from a timing that the engine is put in the cylinder-distribution stable region. These contents are checked at the steps S125 and S126.

D) The ECM 2 decides that the engine 1 is not misfiring, and a delay time DELAY4# has elapsed from a timing that the ECM 2 cancels the misfire decision. These contents are checked at the steps S127 and S128.

E) Exhaust Gas Recirculation (EGR) control executed by the EGR system 58 is being forbidden, and a delay time DELAY5# has elapsed from a start timing of forbidding the EGR. These contents are checked at the steps S129 and S130.

F) The swirl control valve 51 is closed, or a delay time DELAY6# has elapsed from a timing that the swirl control valve 51 is opened. The content is checked at the step S131.

G) The automatic transmission 60 is being set at a lockup condition, and a delay time DELAY7# has elapsed from a timing that the start of the lockup. These contents are checked at the steps S132 and S133.

H) The fuel cut is not being executed, and a delay time DELAY3# has elapsed from a timing of the recovery of the fuel cut. These contents are checked at the steps S134 and S135.

When all of the above conditions are satisfied, the routine of the flowchart shown in FIG. 42 proceeds to a step S136 wherein the ECM 2 decides that the execution of the estimation of the fuel property is allowed and sets an estimation allowance flag at 1 (EAF=1). When at least one of the above conditions is not satisfied, the routine of the flowchart shown in FIG. 42 proceeds to a step S137 wherein the ECM 2 decides that the execution of the estimation of the fuel property is forbidden and sets the estimation allowance flag EAF at 0 (EAF=0).

The conditions (A) to (H) are simply cited after due consideration for wide use of various engines and vehicles. Accordingly, some conditions are not required in some engines and vehicles, and therefore in such a case, the unnecessary conditions may be deleted from the decision contents. For example, in case of a vehicle equipped with a manual transmission, the decision as to the condition (G) is not required. In a simplest case, only one condition may be decided for the allowance of the fuel property estimation.

This fourth embodiment is arranged to forbid executing the estimation of the fuel property when the vehicle VE equipped with the engine 1 is put in at least one of the following conditions: (a) a condition that the purging operation is being executed, (b) a condition that the brake switch is turned ON, (c) a condition of the cylinder-distribution unstable region, (d) a condition of misfire decision, (e) a condition of EGR, (f) a condition that the swirl control valve has just been switched, (g) a condition of non-lockup state, and (h) a condition of fuel cut. The reason for forbidding the estimation of the fuel property in the above-mentioned conditions is that in these conditions the exhaust air-fuel ratio is fluctuated by factors except for the fuel property. Accordingly, if the sampling of the output data as to the exhaust air-fuel ratio is executed even under the above-mentioned condition to be forbidden, the accuracy of the sampled date is largely degraded. This degradation of the data also degrades the accuracy of the estimation of the fuel property.

Hereinafter, the influences of the above-mentioned conditions (a) to (g) will be discussed in detail.

As to the condition (a):

The evaporative emission control system 54 is installed to the vehicle VE equipped with an internal combustion engine 1. The evaporative emission control system 54 is arranged to lead fuel vapor evaporated in a fuel tank to a canister, to adsorb the fuel vapor to activated carbon in the canister, and to purge the adsorbed fuel vapor into the engine by opening a purge value under a predetermined engine operating condition. By opening the purge valve, the canister is communicated with a downstream side of a throttle valve in an intake pipe. Since vacuum pressure is applied to the canister by this opening, fresh air is supplied to the canister so as to release the adsorbed fuel vapor and to feed the released fuel vapor to the engine. Accordingly, when the vehicle VE equipped with the evaporative emission control system 54 is started after it was parked for a relatively long period, the exhaust air-fuel ratio during a first purging operation of the evaporative emission control system 54 becomes richer than that during a period when the purging operation is forbidden.

As to the condition (b):

A so-called Hydro-vac, which is a kind of a hydro vacuum brake system and installed to a brake system, is arranged such that when a brake pedal is not depressed, a vacuum pressure generated downstream of the throttle valve is applied to two chambers formed by dividing a power cylinder by means of a power piston so as to assisting a braking performance of a brake system. Further, when the brake pedal is depressed, one of the two chambers is connected to atmosphere by switching a valve installed thereto. By this valve operation, a pressure difference is produced between the two chambers and therefore the power piston is moved to move a hydraulic piston connected to a tip end of a push rod of the power piston. This movement of the hydraulic piston intensifies a hydraulic pressure supplied from a master cylinder. The intensified hydraulic pressure is supplied to each wheel cylinder. Further, there is a so-called Master-vac for increasing a pushing force of the master cylinder at this side of the master cylinder. This Master-vac employs a pressure increasing principle as same as that of the Hydro-vac. Each of Hydro-vac and Master-vac is a brake booster utilizing a vacuum pressure generated at a downstream side of the throttle valve. Accordingly, when a brake pedal of the brake system 56 of the vehicle VE employing the above-mentioned booster is depressed, the intake vacuum pressure is fluctuated by the operation of the brake booster. Therefore, the quantity of the wall-flow fuel is varied by this fluctuation of the intake vacuum pressure, and therefore the exhaust air-fuel ratio under the operating condition of the brake booster becomes leaner than that under the inoperative condition of the brake booster. The operating condition of the brake booster can be decided by checking the brake switch of the brake system 56. That is, when the brake switch of the brake system 56 is turned on, it is decided that the brake booster is operating. Further, when the brake switch of the brake system 56 is turned off, it is decided that the brake booster is not operating.

As to the condition (c):

Some engines are arranged to previously determine the cylinder-distribution unstable region by the load of the engine and the engine rotation speed treating as a parameter. This cylinder-distribution unstable region is a region where the air-fuel ratio becomes unstable due to the cylinder distribution. The engine 1 employed in this embodiment is arranged to previously determine the cylinder-distribution unstable region by the load of the engine and the engine rotation speed treating as a parameter. Therefore, when the engine 1 is put in the cylinder-distribution unstable region, the exhaust air-fuel ratio under the cylinder-distribution unstable region fluctuates into rich side or lean side. The decision as to the cylinder-distribution unstable region is executed by the ECM 2 on the basis of the information indicative of the vehicle operating condition.

As to the condition (d):

Generally, misfire of an engine includes a rich misfire and lean misfire, and therefore the exhaust air-fuel ratio during misfire of the engine fluctuates rich side or lean side. The ECM 2 of this embodiment is arranged to decide whether the misfire is generating or not. That is, the engine 1 of the vehicle VE is equipped with an engine diagnosis system including a misfire decision process. Therefore, it is possible to forbid the estimation of the fuel property when it is decided that the engine 1 is misfiring.

As to the condition (e):

Engines are generally arranged to execute the EGR control in order to decrease the emission of NOx. EGR gases include unburned components and inactive gases, and therefore the exhaust air-fuel ratio during the EGR control becomes unstable and fluctuates into lean side and rich side as compared with the air-fuel ratio during the EGR forbidding period. As is clear from FIG. 1, the ECM 2 is coupled to the EGR system 58 for executing EGR control. Further, the ECM 2 is arranged to check the condition (e) from an EGR execution indicative signal from the EGR system 58.

As to the condition (f):

Some engines comprise a swirl control valve in intake ports for the purpose of improving combustions during low load condition of the engine. When the swirl control valve are closed, the quantity of the wall-flow fuel is varied. That is, a speed of air in the intake port is increased by closing the swirl control valve, and therefore the quantity of the wall-flow of the fuel is decreased. Accordingly, the switching between open and close of the swirl control valve affects the exhaust air-fuel ratio. As is clear from FIG. 1, the engine 1 comprises the swirl control valve 51 connected to the operation switch 52. The operation switch 52 is coupled to the ECM 2 and sends a signal indicative of the operating state of the swirl control valve 52 to the ECM 2. Therefore, the ECM 2 can check the condition (f) from the switching between open and close of the swirl control valve 51.

As to the condition (g):

The engine 1 of the vehicle VE is coupled to the automatic transmission 60 with a lockup mechanism. Therefore, the engine rotation speed in non-lockup state quickly rises up and quickly falls down as compared with the engine rotation speed in a lockup state. That is, the exhaust air-fuel ratio in the non-lockup state tends to be unstable and fluctuates into lean side and rich side as compared with that in the lockup state. The ECM 2 is arranged to detect the lockup state of the torque converter of the automatic transmission 60.

As to the condition (h):

Some engines are arranged to execute a so-called fuel cut for stopping fuel supplied during deceleration of a vehicle in order to improve fuel consumption. In case of this type engine, the quantity of the wall-flow fuel is varied during the fuel cut operation and just after the recovery of the fuel cut operation, and therefore the exhaust air-fuel ratio is affected during these periods. The engine 1 is arranged to execute the fuel cut according to the vehicle operating condition. The ECM 2 is arranged to decide whether the fuel cut is executed or not. Therefore, the ECM 2 the ECM 2 can check the condition (h).

In the flowchart of FIG. 42, the steps S122, S124, S126, S128, S130, S131, S133 and S135 are provided in order to check whether each of the delay times c to DELAY#8 has elapsed or not. The reason for including the steps for checking various delay times as a forbidding period is that the exhaust air-fuel ratio is unstable during the time period just after the various forbidden conditions (A) to (H) have elapsed. Therefore, during these time periods, the estimation of the fuel property is forbidden. As is clear from the above explanation, the time period includes the time period DELAY#1 just after the forbidding of the purging operation, the time period DELAY#2 just after the turn off of the brake switch, the time period DELAY#3 just after the shifting to the cylinder-distribution stable region, the time period DELAY#4 just after finishing the misfire, the time period DELAY#5 just after forbidding the EGR, the time period DELAY#6 just after the switching of the swirl control valve, the time period DELAY#7 just after the lockup, and the time period DELAY#8 just after the recovery of the fuel cut. Practical time length of each delay time is determined by executing various tests for matching procedures.

The ECM 2 decides whether the purging operation is forbidden or not, on the basis of an output single to a purge valve of the evaporative emission control system 54. The ECM 2 decides whether the EGR control is forbidden or not, on the basis of an output signal to an EGR valve of the EGR system 58. The ECM 2 decides whether the swirl control valve 51 is operating of not, on the basis of an output signal from the operation switch 52. The ECM 2 decides whether the automatic transmission 60 is put in the lockup state or not, on the basis of an output single to a solenoid for varying the state of the lockup clutch of the automatic transmission 60. The ECM 2 decides whether the engine 1 is put in the cylinder-distribution stable region or not, on the basis of an operating point decided by the engine load and the engine rotation speed and a previously prepared map indicating the cylinder-distribution stable region. The ECM 2 decides whether the misfire is generating or not from the result of a misfire decision program executed by the ECM 2. The ECM 2 decides whether the fuel cut is being executed or not, and whether the recovery of the fuel cut has executed, from the result of the fuel injection control program executed by the ECM 2.

That is, if the sampling of the output data as to the exhaust air-fuel ratio is executed even under conditions where the exhaust air-fuel ratio fluctuates, the accuracy of the sampled date is largely degraded. This degradation of the data also degrades the accuracy of the estimation of the fuel property. Accordingly, the present embodiment is arranged to forbid the sampling of the output data under the above-mentioned forbidden conditions so as to prevent the estimation accuracy from degrading.

After the execution of the flowchart shown in FIG. 42, the routine returns to the step S82 wherein the ECM 2 checks the estimation allowance decision flag EAF and decides whether EAF=1 or not. When the decision at the step S64 is negative (EAF=0), that is, when it is decided that the estimation of the fuel property is forbidden, the routine proceeds to a step S93.

At the step S83, the ECM 2 sets the sampling number SA1 at 0 (SA1←0). At a step S84 following to the step S83, the ECM 2 deletes all of the stored data of the exhaust air-fuel ratio and the actual injection pulse width. The reason for initializing the sampling number SA1 at 0 and deleting all of the stored data is that the analysis of the response wave-form of the exhaust air-fuel ratio requires a date for a predetermined period from start to end of the transient, and that if inaccurate data is included in the stored data, the accuracy of the analysis is degraded.

On the other hand, when the decision at the step S82 is affirmative (EADF=1), that is, when it is decided that the estimation of the fuel property is allowed, the routine proceeds to a step S7 which is the same of the first embodiment in order to execute the estimation of the fuel property.

Next, a fifth embodiment of the fuel property detecting system will be discussed.

Basic construction of the fifth embodiment is as same as that of the first embodiment as shown in FIG. 1. Further, the routine for the fuel property estimation of the fifth embodiment employs the routine shown by the flowchart of FIG. 28 of the fifth embodiment. Further, the fifth embodiment employs the fuel property switching decision procedure shown in the flowchart of FIG. 24 employed in the second embodiment.

That is, the fifth embodiment is arranged to employ intermediate fuel having an intermediate volatility as a reference fuel, in contrast to the fourth embodiment in which heavy fuel having a low volatility is employed. Further, in this fifth embodiment, gasoline having a higher volatility with respect to the reference fuel is defined as light gasoline, and gasoline having a lower volatility with respect to the reference fuel is defined as heavy gasoline. In the procedure for deciding the fuel property, a difference between the cutoff frequency of the plant model and the cutoff frequency of the norm model is calculated, and the fuel property of the practically used gasoline is decided by comparing the difference between the cutoff frequencies and a tolerance (allowable range) thereof. By providing the tolerance, even if the cutoff frequency of the fuel to be decided is dispersed with respect to that of the reference fuel, it becomes possible to decide the fuel property of the practically used fuel. As is the same as the second embodiment, it is necessary in the fifth embodiment to previously provide table values necessary for calculating the post-start increase correction coefficient KAS by each of the three kinds of fuels in correspond to graphs of FIGS. 18 to 22.

Referring to FIGS. 29 to 35, there is shown a sixth embodiment of the fuel property estimating system according to the present invention. The sixth embodiment is generally the same as the fourth embodiment except that the fuel property switching decision procedure as same as that shown by the flowchart of FIG. 26 of the third embodiment is employed. That is, instead of the steps S8 and S9, steps S71 and S72, which are the same as those shown in FIG. 25 of the third embodiment. Therefore, the explanation of the changed step S71 and S72 is omitted herein. Further, as shown by a flowchart of FIG. 30, the KAS calculation procedure of the sixth embodiment is partially different from the flowchart of FIG. 17. Steps as same as those of FIG. 17 in the first are denoted by same step reference numerals. Explanation as to different steps S91, S92, S93, S94, S95 and S96 from the corresponding steps of the flowchart of FIG. 17 will be made hereinafter.

At the step S91, the ECM 2 reads the fuel property estimate FC estimated in the subroutine of the fuel property estimation as same as that of the flowchart shown in FIG. 26 of the third embodiment.

Figure 31:
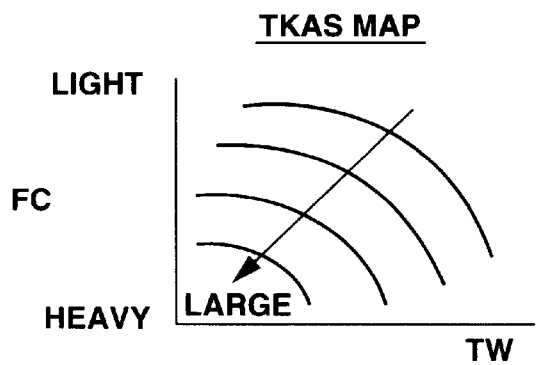
FIG. 31 is a graph showing a characteristic of TKAS with respect to the fuel property and a cooling water temperature.

At the step S92 following to the step S42, the ECM 2 calculates TKAS by retrieving a table corresponding to a map of FIG. 31 from the deteted cooling water temperature Tw and the fuel property estimate.

Figure 32:
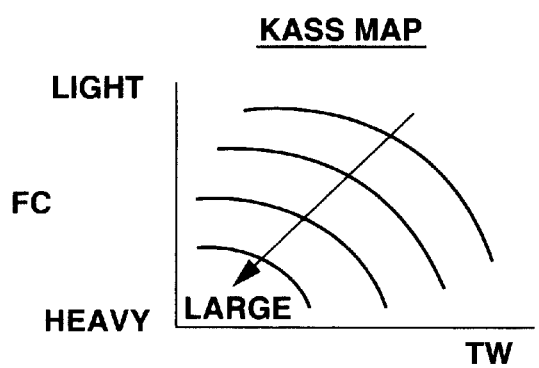
FIG. 32 is a graph showing a characteristic of KASS with respect to the fuel property and the cooling water temperature.

At a step S93 following to the step S92, the ECM 2 calculates KASS by retrieving a table corresponding to a map of FIG. 32 from the cooling water temperature Tw and the fuel property estimate.

Figure 33:
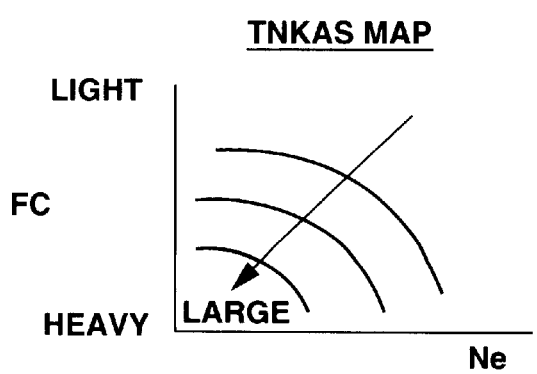
FIG. 33 is a graph showing a characteristic of TNKAS with respect to the fuel property and an engine rotation speed.

At a step S94 following to the step S92, the ECM 2 calculates TNKAS by retrieving a table corresponding to a map of FIG. 33 from the detected engine rotation speed Ne and the fuel property estimate.

Figure 34:
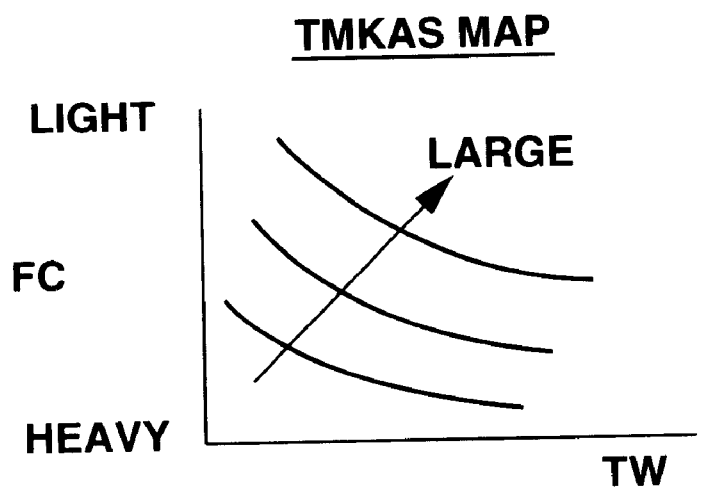
FIG. 34 is a graph showing a characteristic of TMKAS with respect to the fuel property and the cooling water temperature.

Further, at the step S95 following to a negative decision at the step S42, the ECM 2 calculates TNKAS by retrieving a table corresponding to a map of FIG. 34 from the cooling water temperature Tw and the fuel property estimate.

Figure 35:
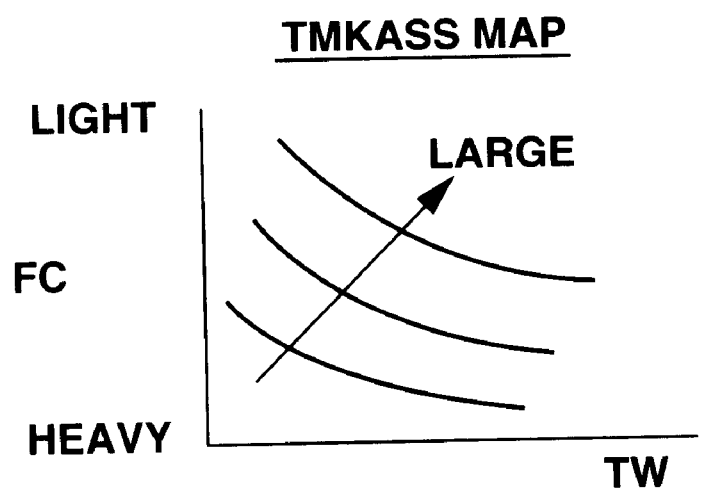
FIG. 35 is a graph showing a characteristic of TMKASS with respect to the fuel property and the cooling water temperature.

Additionally, at the step S96 following to the step S52, the ECM 2 calculates TMKASS by retrieving a table corresponding to a map of FIG. 35 from the cooling water temperature Tw and the fuel property estimate.

As clearly shown in FIGS. 31 and 32, TKAS and KASS respectively take smaller values according to the lowering of the cooling water temperature Tw under a constant fuel property FC, and take larger values according to the change of the fuel property from light to heavy under a constant cooling water temperature Tw. Further, as shown in FIGS. 34 and 35, TMKAS and TMKASS respectively take larger values according to the increase of the cooling water temperature Tw under a constant fuel property FC, and take larger values according to the switching of the fuel property from heavy to light under a constant cooling temperature Tw. Furthermore, when the fuel property estimate and the cooling water temperature are constant, TKAS is larger than KASS, and TMKAS is larger than TMKASS.

In the thus arrange sixth embodiment, table values employed for calculating the post-start increase correction coefficient KAS are determined according to the fuel property estimate FC which is treated as continuously values. Therefore, the calculation accuracy of the post-start increase correction coefficient KAS is further improved.

Referring to FIGS. 36 to 41, there is shown a seventh embodiment of the fuel property estimating system according to the present invention.

Figure 30:
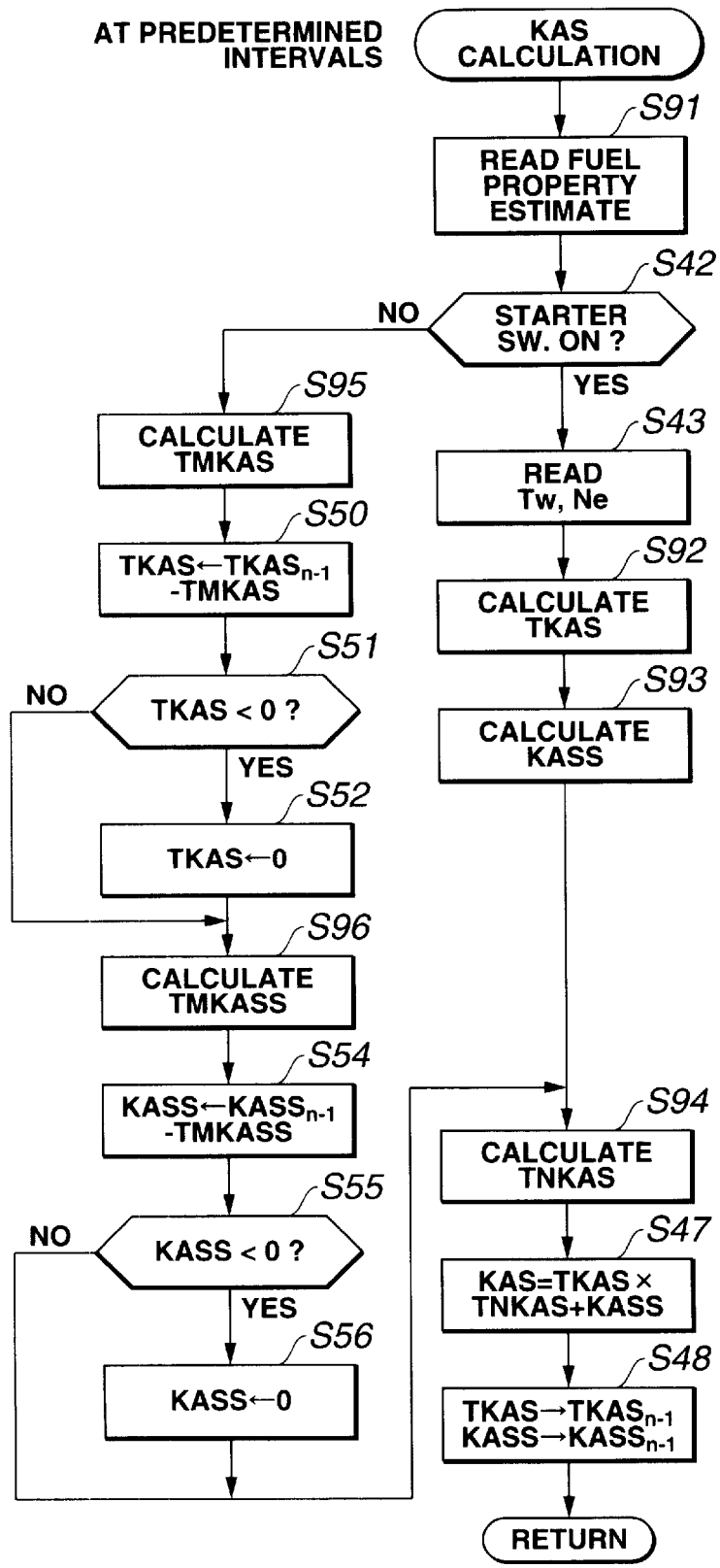
FIG. 30 is a flowchart employed for explaining the calculation of the post-start increase correction coefficient of the sixth embodiment.
Figure 36:
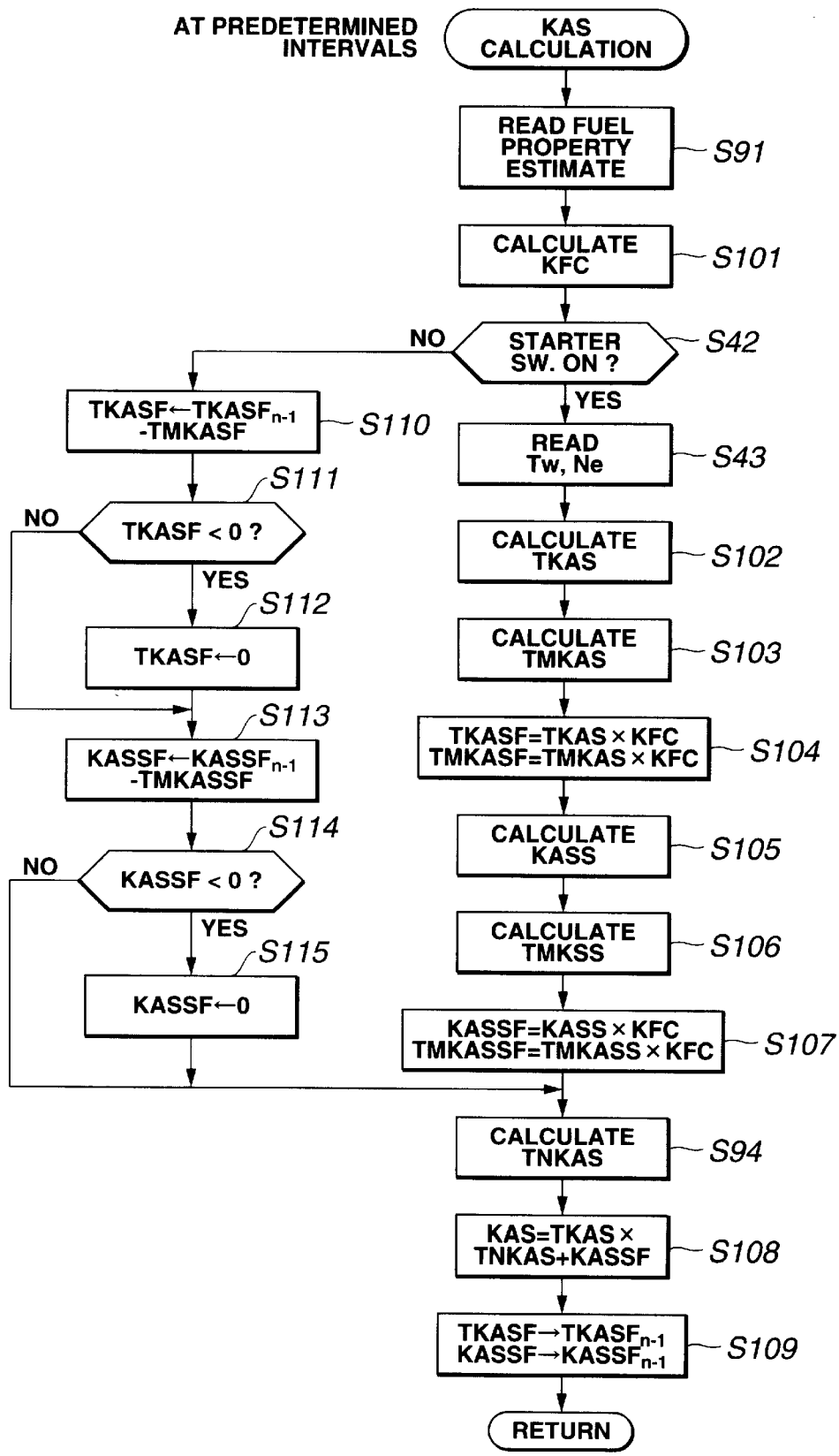
FIG. 36 is a flowchart employed for explaining the calculation of the post-start correction increase coefficient KAS of the sixth embodiment.

The seventh embodiment is generally as same as the sixth embodiment except that the KAS calculation procedure shown in FIG. 36 is employed instead of that shown in FIG. 30. This seventh embodiment is arranged so as to decrease the steps for calculating KAS by employing a fuel property correction value KFC corresponding to the fuel property estimate FC, by correcting data matched with heavy-most gasoline by means of the employed fuel property correction value KFC, and by calculating the post-start increase correction coefficient KAS on the basis of the corrected data. More specifically, steps S101 and S102 to S115 are newly added in the KAS calculation of the seventh embodiment.

Figure 37:
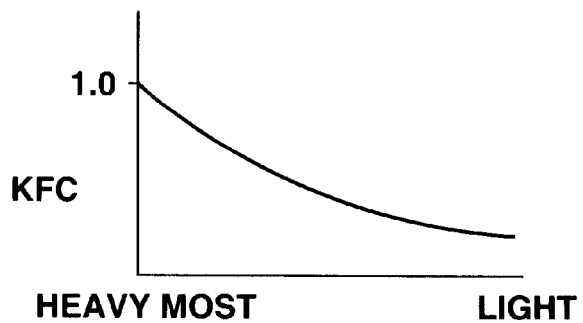
FIG. 37 is a graph showing a relationship between the fuel property and a fuel property correction value.

At the step S101 following to the step S91, the ECM 2 calculating the fuel property correction value KFC by retrieving a table corresponding to the graph of FIG. 37 from the fuel property estimate FC. As shown in FIG. 37, the fuel property correction value KFC takes a maximum value 1.0 when the fuel property is heavy most, and is gradually decreased according to the switching of the fuel property from the heavy to light.

Figure 38:
FIG. 38 is a graph showing a relationship between the cooling water temperature and the post-start increase water temperature correction value TKAS.

At the step S102 following to the step S43, the ECM 2 calculates TKAS matched with heavy-most gasoline by retrieving a table corresponding to a graph of FIG. 38 from the cooling water temperature Tw.

Figure 39:
FIG. 39 is a graph showing a relationship between the cooling water temperature and the post-start increase decreasing time rate TMKAS.

At the step S103, the ECM 2 calculates TMKAS matched with heavy most gasoline by retrieving a table corresponding to a graph of FIG. 39 from the cooling water temperature Tw.

At the step S104, the ECM 2 calculates a post-start increase water temperature correction value TKASF corresponding to the fuel property and a post-start increase decreasing time rate TMKASF corresponding to the fuel property from the calculated TKAS and TMKAS and the following equations (38-1) and (38-2):

$$TKASF = TKAS \times KFC \qquad (38\text{-}1)$$

$$TMKASF = TMKAS \times KFC. \qquad (38\text{-}2)$$

Figure 40:
FIG. 40 is a graph showing a relationship between the cooling water temperature and the second post-start increase correction coefficient KASS.

At the step S105, the ECM 2 calculates KASS matched with heavy most gasoline by retrieving a table corresponding to a graph of FIG. 40 from the cooling water temperature Tw.

Figure 41:
FIG. 41 is a graph showing a relationship between the cooling water temperature and the second post-start increase decreasing time rate TMKASS.

At the step S106, the ECM 2 calculates TMKASS matched with heavy most gasoline by retrieving a table corresponding to a graph of FIG. 41 from the cooling water temperature Tw.

At the step S107, the ECM 2 calculates a second post-start increase water temperature correction value TKASDF corresponding to the fuel property and a second post-start increase decreasing time rate TMKASSF corresponding to the fuel property from the calculated TKASS and TMKASS and the following equations (39-1) and (39-2):

$$TKASF = TKAS \times KFC \qquad (39\text{-}1)$$

$$TMKASF = TMKAS \times KFC. \qquad (39\text{-}2)$$

Further, at the step S108 following to the step S94, the ECM 2 calculates KAS from the calculated KASSF, TNKAS, TMKASSF and the following equation (40):

$$KAS = TKASF \times TNKAS + KASSF. \qquad (40)$$

At the step S109, the ECM 2 stores the calculated correction values TKAS and KASS in addressed portions TKAS$_{n-1}$ and KASS$_{n-1}$ of the EEPROM so that the ECM 2 correctly operates even if the starter switch is turned OFF.

In the next routine, the starter switch is turned OFF, that is, the engine 1 has been started, the routine proceeds from the step S42 to the step S110 to execute an attenuating operation.

As the step S110, the ECM 2 calculates a present-time post-start increase water temperature correction value TKASF corresponding to heavy most gasoline by subtracting the calculated TMKASF from the previous time post-start increase water temperature correction value TKASF$_{n-1}$ (TKASF←TKASF$_{n-1}$-TMKASF).

At the step S111, the ECM 2 decides whether TKASF<0 or not. When the decision at the step S111 affirmative, the routine proceeds to a step S112 wherein the post-start increase water temperature correction value TKASF corresponding to heavy most gasoline is set at zero (TKASF←0). When the decision at the step S111 is negative, the routine proceeds to a step S113. At a time just after the starter switch was turned off, TKASF>0. Therefore, at that time the routine proceeds to the step S113.

As the step S113, the ECM 2 calculates a present-time second post-start increase correction value KASSF corresponding to heavy most gasoline by subtracting the calculated TMKASSF from the previous-time second post-start increase correction value KASSF$_{n-}$(KASSF←KASSF$_{n-1}$-TMKASSF).

At a step S114, the ECM 2 decides whether KASSF<0 or not. When the decision at the step S114 affirmative, the routine proceeds to a step S115 wherein KASSF is set at zero (KASSF←0) and then proceeds to the step S94. When the decision at the step S114 is negative, the routine proceeds to a step S94.

When the fuel property of gasoline in use is near light gasoline rather than heavy gasoline, KFC becomes smaller than 1.0, and therefore TKAASF<TKAS, TMKASF<TMKAS, KASSF<KASS and TMKASSF<TMKASS. Accordingly, in this state of the fuel property, the calculated KAS takes a value smaller than that of the heavy most gasoline. Consequently, as is similar to FIG. 30, an optimum post-start increase correction coefficient is given for gasoline which is lighter than heavy most gasoline in fuel property. Furthermore, when heavy most gasoline is practically employed, KFC=1.0, and therefore TKAASF=TKAS, TMKASF=TMKAS, KASSF=KASS and TMKASSF=TMKASS. Accordingly, in this state, the calculated KAS takes a value as same as that of the heavy most gasoline.

With the thus arranged seventh embodiment, the data necessary for the calculation of KAS is obtained only by matching the characteristics shown in FIGS. 38 to 41 with respect to heavy most gasoline. This largely facilitates calculation steps as compared with those of the sixth embodiment.

Although the fourth, sixth and seventh embodiments according to the present invention have been shown to employ (A) the fuel property switching flag, (B) the fuel property estimate FC and (C) the fuel property correction value KFS, respectively, with respect to the post-start increase correction coefficient KAS corresponding to the fuel injection quantity correction value, it will be understood that the present invention is not limited to these. For example, the injection quantity correction value of (1) low frequency component (wall-flow fuel), (2) high frequency component (wall-flow fuel), (3) water temperature increase correction quantity, (4) non-burnt increase correction quantity, and the fuel injection quantity of (5) start fuel injection quantity, (6) acceleration interrupt injection quantity may be adapted to the respective cases (A), (B) and (C).

Japanese Patent Provisional Publication No. 10-18882 discloses detailed explanations as to the above (1) and (2). Japanese Patent Provisional Publication No. 10-18883 discloses detailed explanations as to the above (3) and (4). Japanese Patent Provisional Publication No. 7-63082 discloses a detailed explanation as to the above (5). Japanese Patent Provisional Publication No. 64-3245 discloses a detailed explanation as to the above (6).

Although the embodiments according to the present invention have been shown and described such that the plant model of the fuel in use is identified by sampling the response wave-form of the exhaust air-fuel ratio in response to the fuel injection quantity during the transient period and controlling the parameter of the plant model constructed in the ECM 2 so as to minimize the prediction error between the plant model and the norm model of reference fuel, it will be understood that the present invention is not limited to this. For example, a fuel supply quantity may be employed as an input instead of the fuel injection quantity. Further, instead of the control for minimizing the prediction error, a control for decreasing the prediction error may be employed.

The entire contents of Japanese Patent Applications Nos. 11-98709 filed on Apr. 6, 1999 and 11-06659 filed on Apr. 14, 1999 in Japan are incorporated herein by reference.

Although the invention has been described above by reference to certain embodiments of the invention, the invention is not limited to the embodiments described above. Modifications and variations of the embodiments described above will occur to those skilled in the art, in light of the above teaching. The scope of the invention is defined with reference to the following claims.

What is claimed is:

1. A fuel property detecting system for an internal combustion engine, comprising:
   a fuel injector installed to the engine and injecting a quantity of fuel to the engine;
   an air-fuel sensor installed to an exhaust passage of the engine and detecting an exhaust air-fuel ratio; and
   a control unit coupled to said fuel injector and said air-fuel sensor, said control unit being arranged
      to calculate the quantity of fuel injected from said fuel injector according to an operating condition of the engine,
      to command said fuel injector to inject the calculated quantity of fuel,
      to sample data of a response wave-form of the exhaust air-fuel ratio in response to the injected quantity of fuel at a transient period,
      to identify a plant model as to fuel in use by controlling a parameter of a previously constructed plant model on the basis of the sampled data so as to decrease a prediction error between the plant model and a norm model,
      to calculate a cutoff frequency of the identified plant model, and
      to estimate a fuel property of the fuel in use from the calculated cutoff frequency of the identified plant model and data previous stored in said control unit.

2. The fuel property detecting system as claimed in claim 1, wherein said control unit estimates the fuel property of the employed fuel by comparing the cutoff frequency of the identified plant model and a cutoff frequency of the norm model.

3. The fuel property detecting system as claimed in claim 1, wherein said control unit estimates the fuel property of the fuel in use by comparing a difference between the cutoff frequency of the identified plant model and a cutoff frequency of the norm model with a tolerane.

4. The fuel property detecting system as claimed in claim 1, wherein said control unit estimates the fuel property of the fuel in use by calculating a fuel property estimate from the calculated cutoff frequency and a characteristic of the fuel property estimate with respect to the cutoff frequency which characteristic is previously provided in said control unit.

5. The fuel property detecting system as claimed in claim 1, wherein said control unit is further arranged to decide whether the engine operating condition is put in an exceptional fluctuating region where the exhaust air-fuel ratio fluctuates due to a factor except for the fuel property and to forbid sampling the data when the engine operating condition is put in the exceptional fluctuating region.

6. The fuel property detecting system as claimed in claim 1, wherein said control unit is further arranged to calculate the fuel supply quantity on the basis of the estimated fuel property.

7. The fuel property detecting system as claimed in claim 1, wherein said control unit stores an estimation result of the fuel property in a non-volatile memory.

8. The fuel property detecting system as claimed in claim 2, wherein said control unit is arranged to decide that the fuel property of the fuel in use is lighter than that of a reference fuel when the norm model is matched with the reference fuel and when the cutoff frequency of the identified plant model is higher than a cutoff frequency of the norm model.

9. The fuel property detecting system as claimed in claim 3, wherein said control unit is arranged to decide that the fuel property of the employed fuel is lighter than that of a reference fuel when the norm model is matched with the reference fuel, when a difference between the cutoff frequency of the identified plant model and a cutoff frequency of the norm model is out of a tolerance, and when the cutoff frequency of the identified plant model is higher than a cutoff frequency of the norm model.

10. The fuel property detecting system as claimed in claim 1, wherein decreasing the prediction error during the identification of the plant model includes minimizing the prediction error.

11. The fuel property detecting system as claimed in claim 1, wherein the plant model is constructed by a fuel behavior model, an exhaust model and a dead time.

12. The fuel property detecting system as claimed in claim 11, wherein the fuel behavior model is expressed by a second-order time-lag system model constructed by a quadratic denominator and a quadratic numerator.

13. The fuel property detecting system as claimed in claim 11, wherein the exhaust model is expressed by a first-order time-lag model constructed by a linear denominator.

14. The fuel property detecting system as claimed in claim 11, wherein the dead time is expressed by a sum of an adaptation term, a calculation term and a decision term.

15. The fuel property detecting system as claimed in claim 1, wherein said control unit executes a batch-processing least squares method employing ARX model as an identification method of the plant model.

16. The fuel property detecting system as claimed in claim 1, wherein the estimation of the fuel property is executed once in a period from start to stop of the engine.

17. The fuel property detecting system as claimed in claim 1, further comprising a detector unit for detecting the engine operating condition.

18. The fuel property detecting system as claimed in claim 17, wherein said detector unit includes a detector further comprising a rotation speed detector for detecting an engine rotation speed, an airflow meter for measuring intake air supplied to the engine, a throttle opening detector for detecting an opening of a throttle valve, and a water temperature detector for detecting a cooling water temperature of the engine.

19. The fuel property detecting system as claimed in claim 1, wherein the transient period of the operation of the engine is produced by applying a trigger signal to the input.

20. The fuel property detecting system as claimed in claim 5, wherein said control unit is coupled to an evaporative emission control system and receives a purging signal when the evaporative emission control system is executing a purging operation by which stored fuel vapor is purged from the evaporative emission control system to the engine, said control unit deciding that the engine is operating in the exceptional fluctuating region when said control unit receives the purging signal.

21. The fuel property detecting system as claimed in claim 20, said control unit decides that the engine is operating in the exceptional fluctuating region when an elapsed time from stopping the purging operation is smaller than a first time period.

22. The fuel property detecting system as claimed in claim 5, wherein said control unit is coupled to a brake system employing a booster of an engine vacuum pressure employing type and receives a braking signal when an braking is executed by using the booster, said control unit deciding that the engine is operating in the exceptional fluctuating region when said control unit receives the braking signal.

23. The fuel property detecting system as claimed in claim 22, said control unit decides that the engine is operating in the exceptional fluctuating region when an elapsed time from stopping the braking is not smaller than a second time period.

24. The fuel property detecting system as claimed in claim 5, wherein said control unit is arranged to decide on the basis of signals indicative of the engine operating condition whether the engine is operating in a cylinder-distribution unstable region, said control unit deciding that the engine is operating in the exceptional fluctuating region when the engine is operating in the cylinder-distribution unstable region.

25. The fuel property detecting system as claimed in claim 24, said control unit decides that the engine is operating in the exceptional fluctuating region when an elapsed time from a time that the operating region of the engine is switched from the cylinder-distribution unstable region to a cylinder-distribution stable region is smaller than a third time period.

26. The fuel property detecting system as claimed in claim 5, wherein said control unit is arranged to decide on the basis of signals indicative of the engine operating condition whether the engine is misfiring, said control unit deciding that the engine is operating in the exceptional fluctuating region when the engine is misfiring.

27. The fuel property detecting system as claimed in claim 26, said control unit decides that the engine is operating in the exceptional fluctuating region when the engine is not misfiring and when an elapsed time from a last misfiring is smaller than a fourth time period.

28. The fuel property detecting system as claimed in claim 5, wherein said control unit is coupled to an exhaust gas recirculation (EGR) system and receives an EGR signal when the EGR system is operating, said control unit deciding that the engine is operating in the exceptional fluctuating region when said control unit receives the EGR signal.

29. The fuel property detecting system as claimed in claim 28, said control unit decides that the engine is operating in the exceptional fluctuating region when an elapsed time from stopping the EGR operation is smaller than a fifth time period.

30. The fuel property detecting system as claimed in claim 5, wherein said control unit is coupled to a swirl control valve and receives a valve state indicative signal which shows an opening state of the swirl control value, said control unit deciding that the engine is operating in the exceptional fluctuating region when an elapsed time from a time that the opening state is changed is smaller than a sixth time period.

31. The fuel property detecting system as claimed in claim 5, wherein said control unit is coupled to an automatic transmission and receives a non-lockup signal indicative that a lockup mechanism of the automatic transmission system is set in a non-lockup state, said control unit deciding that the engine is operating in the exceptional fluctuating region when said control unit receives the non-lockup signal.

32. The fuel property detecting system as claimed in claim 31, said control unit decides that the engine is operating in the exceptional fluctuating region when the lockup converter is being put in the lockup state and when an elapsed time from a time that the lockup mechanism is set in the lockup state is smaller than a seventh time period.

33. The fuel property detecting system as claimed in claim 5, wherein said control unit is arranged to stop supplying fuel to the engine when the engine is put in a predetermined fuel cut condition, said control unit deciding that the engine is operating in the exceptional fluctuating region when fuel supply is stopped.

34. The fuel property detecting system as claimed in claim 33, said control unit decides that the engine is operating in the exceptional fluctuating region when the fuel supply is not stopped and when an elapsed time from a recovery of stopping the fuel supply is smaller than an eighth time period.

35. The fuel property detecting system as claimed in claim 1, wherein said control unit calculates the quantity of fuel injected from said fuel injector on the basis of the estimated fuel property.

36. The fuel property detecting system as claimed in claim 1, wherein the sampled data includes input data of the quantity of fuel injected from said fuel injection and output data of the air-fuel ratio in response to the quantity of injected fuel.

37. A fuel property detecting system comprising:
  means for calculating a fuel supply quantity according to an operating condition of an engine;
  means for supplying the calculated quantity of fuel to the engine;
  means for detecting an exhaust air-fuel ratio of an engine;
  means for sampling data of a response wave-form of an exhaust air-fuel ratio in response to the fuel supply quantity at a transient period;
  means for identifying a plant model as to employed fuel by controlling a parameter of a previously constructed plant model on the basis of the sampled data so as to decrease a prediction error of the plant model with respect to a norm model;
  means for calculating a cutoff frequency of the identified plant model; and
  means for estimating a fuel property of the employed fuel by comparing the cutoff frequency of the identified plant model and a cutoff frequency of the norm model.

* * * * *